US012748091B2

(12) United States Patent
LaFranchi et al.

(10) Patent No.: US 12,748,091 B2
(45) Date of Patent: Sep. 29, 2026

(54) DETECTION OF VOLATILE ORGANIC COMPOUNDS

(71) Applicant: Aclima Inc., San Francisco, CA (US)

(72) Inventors: Brian LaFranchi, Berkeley, CA (US); Rishabh Urvesh Shah, Everett, WA (US); Bassam Samih Dgheim, San Mateo, CA (US); Todd Langland, El Granada, CA (US); Walker Alexander, Rockland, ME (US); Davida Herzl, San Francisco, CA (US); Matthew Hill, San Francisco, CA (US)

(73) Assignee: Aclima Inc., San Leandro, CA (US)

(*) Notice: Subject to any disclaimer, the term of this patent is extended or adjusted under 35 U.S.C. 154(b) by 435 days.

(21) Appl. No.: 18/528,341

(22) Filed: Dec. 4, 2023

(65) Prior Publication Data

US 2024/0183832 A1 Jun. 6, 2024

Related U.S. Application Data

(60) Provisional application No. 63/430,304, filed on Dec. 5, 2022.

(51) Int. Cl.
*G01N 33/00* (2006.01)

(52) U.S. Cl.
CPC ..... *G01N 33/0047* (2013.01); *G01N 33/0037* (2013.01); *G01N 33/004* (2013.01)

(58) Field of Classification Search
None
See application file for complete search history.

(56) References Cited

U.S. PATENT DOCUMENTS

| | | | | |
|---|---|---|---|---|
| 7,360,461 B2 * | 4/2008 | Desrochers | G01N 1/22 73/864.81 |
| 11,719,541 B2 * | 8/2023 | Langland | G01C 21/3848 702/5 |
| 11,781,976 B2 * | 10/2023 | Langland | G01N 33/0004 340/632 |
| 11,788,997 B2 * | 10/2023 | Chou | G01N 33/0006 73/1.06 |
| 11,833,882 B2 * | 12/2023 | Murphy | B60H 1/00978 |

(Continued)

FOREIGN PATENT DOCUMENTS

| | | | | |
|---|---|---|---|---|
| CN | 113156060 A * | 7/2021 | G01C 21/3415 |
| WO | WO-2021057030 A1 * | 4/2021 | G01S 19/14 |

OTHER PUBLICATIONS

Dang et al. "Development of a Multichannel Organics In situ enviRonmental Analyzer (MOIRA) for mobile measurements of volatile organic compounds." EGUsphere 2023 (2023): 1-33.
Healy et al. "Spatially resolved source apportionment of industrial VOCs using a mobile monitoring platform." Atmosphere 13.10 (2022): 1722.

(Continued)

*Primary Examiner* — Daniel S Larkin
(74) *Attorney, Agent, or Firm* — Van Pelt, Yi & James LLP

(57) ABSTRACT

Detection of volatile organic compounds (VOCs) is disclosed, including: receiving mobile sensor data, wherein the mobile sensor data includes volatile organic compounds (VOC) sensor data and non-VOC sensor data; identifying VOC peaks in the VOC sensor data; identifying non-VOC peaks in the non-VOC sensor data; correlating the VOC peaks with the non-VOC peaks; and determining a source type associated with the VOC peaks based at least in part on the correlation between the VOC peaks and the non-VOC peaks.

20 Claims, 16 Drawing Sheets

(56) References Cited

U.S. PATENT DOCUMENTS

| | | | | |
|---|---|---|---|---|
| 2015/0253300 | A1* | 9/2015 | Zanfei | G01N 33/0075 702/24 |
| 2016/0190979 | A1* | 6/2016 | Wildes | H02S 20/24 136/251 |
| 2020/0271277 | A1* | 8/2020 | Lewis | G05D 1/0202 |
| 2020/0327111 | A1* | 10/2020 | Smith | G01R 33/54 |
| 2021/0010929 | A1* | 1/2021 | Langland | G01D 21/02 |
| 2022/0291184 | A1* | 9/2022 | Lunden | G01N 33/0027 |
| 2023/0288390 | A1* | 9/2023 | Lunden | G01N 33/0047 |

OTHER PUBLICATIONS

Huang et al. "Mobile monitoring of VOCs and source identification using two direct-inlet MSs in a large fine and petroleum chemical industrial park." Science of The Total Environment 823 (2022): 153615.

Li et al. "High-density volatile organic compound monitoring network for identifying pollution sources." Science of The Total Environment 855 (2023): 158872.

Liang et al. "Imaging VOC distribution in cities and tracing VOC emission sources with a novel mobile proton transfer reaction mass spectrometer." Environmental Pollution 265 (2020): 114628.

Ren et al. "A novel mobile navigation monitoring system based on single photon ionization time-of-flight mass spectrometry: Instrumentation development, performance and application." Vacuum 203 (2022): 111316.

* cited by examiner

DETECTION OF VOLATILE ORGANIC COMPOUNDS

CROSS REFERENCE TO OTHER APPLICATIONS

This application claims priority to U.S. Provisional Patent Application No. 63/430,304 entitled DETECTION AND ANALYSIS OF AIR TOXICS filed Dec. 5, 2022 which is incorporated herein by reference for all purposes.

BACKGROUND OF THE INVENTION

Volatile Organic Compounds (VOCs) are chemicals that are of interest to be detected because they are potential contaminants in air and may be both acutely and chronically hazardous, particularly if emitted in high enough amounts. Health hazards of VOCs include serious respiratory issues, neurological issues, reproductive and developmental issues, and cancer. They may also lead to secondary formation of other hazardous air pollutants such as fine particulate matter (PM2.5) and ozone (O3). The Environmental Protection Agency (EPA) maintains a list of 188 hazardous air pollutants that it seeks to reduce emissions of under the Clean Air Act, and most of these pollutants fall into the category of VOCs. Some examples of these hazardous VOCs include BTEX chemicals (benzene, ethylbenzene, toluene, and xylene). Although emission of VOCs may be legal, the emission is also typically regulated. While regulatory authorities may grant permits to businesses to emit certain hazardous VOCs, the impact of these emissions is often not well understood, including the locations impacted and the concentrations at those locations. Additionally, in complex urban and industrial environments, there are typically many sources of VOC emissions that are not permitted and/or not known to be a concern by the regulators. Determining the geographic distribution of VOC pollution in a particular region typically requires deployment of expensive instrumentation, operated by experts and can only be done on very small scales. Thus, capturing and analyzing VOC data for a large region may be time consuming, inefficient, and costly.

BRIEF DESCRIPTION OF THE DRA WINGS

Various embodiments of the invention are disclosed in the following detailed description and the accompanying drawings.

DETAILED DESCRIPTION

Figure 1:
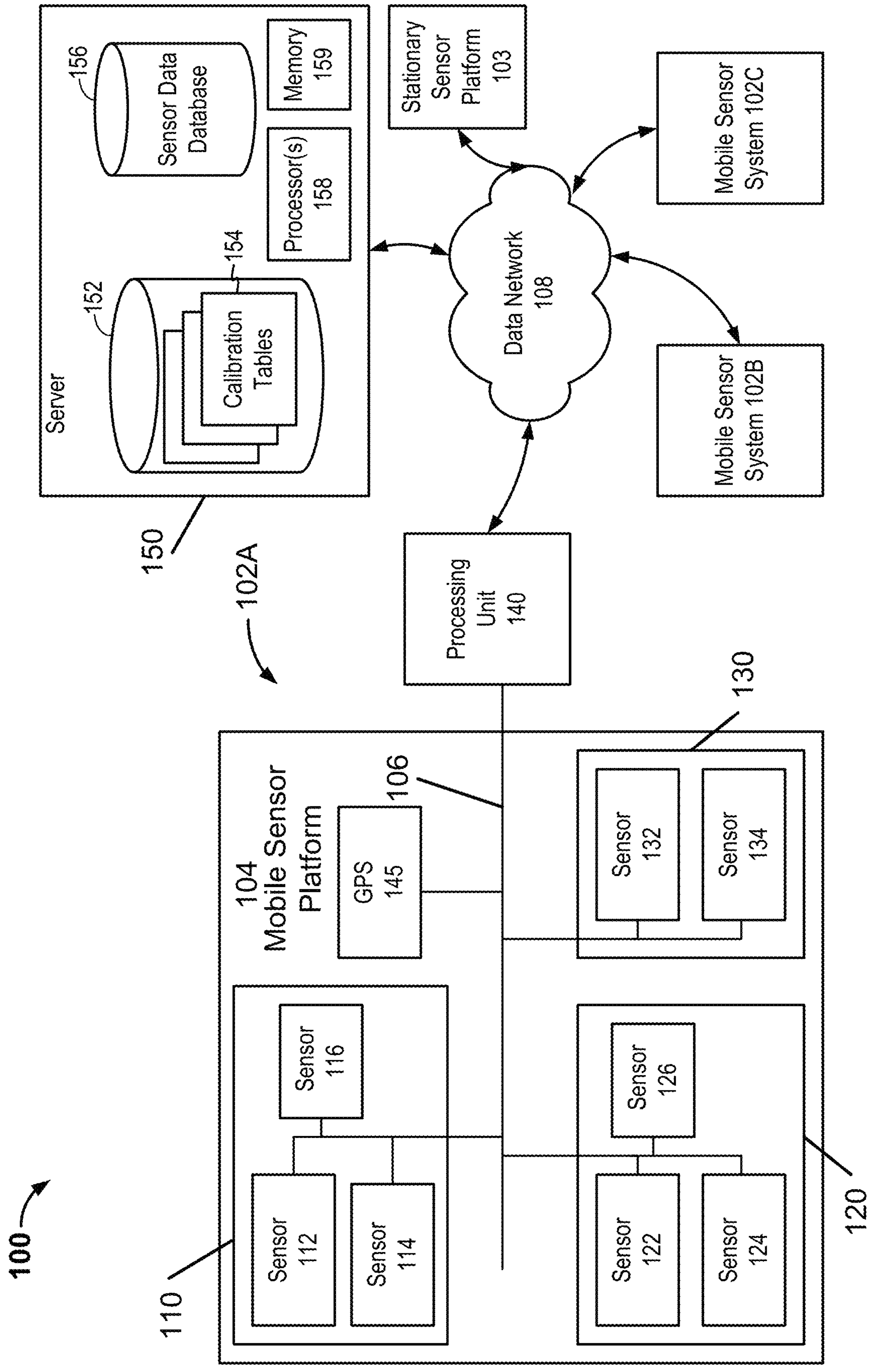
FIG. 1 depicts an embodiment of a system for collecting and processing environmental data.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Embodiments of detection of volatile organic compounds (VOCs) are described herein. The mobile sensor data is received. In various embodiments, the mobile sensor data comprises data streams that are collected by sets of sensors that are located on mobile sensor platforms that are mounted on one or more vehicle(s), such as automobile(s) or drone(s). In various embodiments, each set of sensors comprises a VOC sensor that is configured to detect the presence of at least one type of VOC. In some embodiments, the VOC sensor that is included in each set of sensors is a total VOCs (TVOC) sensor, which detects the presence of any one of multiple types of VOCs. In various embodiments, each set of sensors comprises at least one non-VOC sensor that is configured to detect the presence of a pollutant other than a VOC. Examples of non-VOC pollutants include carbon monoxide, carbon dioxide, nitric oxide, methane, and fine particulate matter. In various embodiments, the mobile sensor data comprises multiple independent sensor data streams that are generated by respective sensors of different types and/or across different vehicles. In various embodiments, a sensor data stream comprises a series of sensor data points (e.g., concentration amounts) with corresponding time and location information associated with each data point. VOC peaks are identified in the received VOC sensor data. Non-VOC peaks are identified in the received non-VOC sensor data. In various embodiments, a VOC peak is determined as a local peak within the data points in its temporal neighborhood. Each VOC peak is associated with at least corresponding time information and location information. In various embodiments, a non-VOC peak is similarly determined and is also therefore associated with at least corresponding time information and location information. The VOC peaks are correlated with the non-VOC peaks. A source type classification associated with the VOC peaks is determined based at least in part on the correlation between the VOC peaks and the non-VOC peaks. In various embodiments, a source type classification of a VOC peak describes the possible type of source or event that led to the VOC peak. The source type classification of a VOC peak could ultimately trigger/inform the type of follow up research (e.g., using more sensitive and specific measurement instruments) that may be performed at the location associated with the VOC peak, for example.

FIG. 1 depicts an embodiment of a system for collecting and processing environmental data. System 100 includes multiple mobile sensor platforms 102A, 102B, 102C and server 150. In some embodiments, system 100 may also include one or more stationary sensor platforms 103, of which one is shown. Stationary sensor platform 103 may be used to collect environmental data at a fixed location. The environmental data collected by stationary sensor platform 103 may supplement the data collected by mobile sensor platforms 102A, 102B and 102C. Thus, stationary sensor platform 103 may have sensors that are the same as or analogous to the sensors for mobile sensor platforms 102A, 102B and 102C. In other embodiments, stationary sensor platform 103 may be omitted. Although a single server (server 150) is shown, multiple servers may be used. The multiple servers may be in different locations. Although three mobile sensor platforms 102A, 102B and 102C are shown, another number are typically present. Mobile sensor platforms 102A, 102B and 102C and stationary sensor platform(s) 103 may communicate with server 150 via a data network 108. The communication may take place wirelessly.

Mobile sensor platforms 102A, 102B, and 102C may be mounted on respective vehicles, such as automobiles or drones. In some embodiments, mobile sensor platforms 102A, 102B, and 102C are desired to stay in proximity to the ground to be better able to sense conditions analogous to what a human would experience. Mobile sensor platform 102A includes a bus 106, sensors 110, 120 and 130. Although three sensors are shown, another number may be present on mobile sensor platform 102A. In addition, a different configuration of components may be used with sensors 110, 120 and 130. Each sensor 110, 120 and 130 is used to sense environmental quality and may be of primary interest to a user of system 100. For example, sensors 110, 120 and 130 may be gas sensors, volatile organic compound (VOC) sensors, particulate matter sensors, radiation sensors, noise sensors, light sensors, temperature sensors, or other analogous sensors that capture variations in the environment. For example, sensors 110 (which in turns includes sensors 112, 114, and 116), 120 (which in turns includes sensors 122, 124, and 126), and 130 (which in turns includes sensors 132 and 134) may be used to sense one or more of $NO_2$, CO, NO, $O_3$, $SO_2$, $CO_2$, VOCs, $CH_4$, $C_2H_6$, particulate matter, black carbon, noise, light, temperature, radiation, other environmental components (e.g. other ambient gas(es)), and/or other parameters. In various embodiments, at least one of sensors 110, 120, and 130 of mobile sensor platform 104 includes a total VOC (TVOC) sensor, which detects the presence of any of several types of VOCs (instead of a single type of VOC). One advantage of using a TVOC sensor is that one TVOC sensor is more cost effective and space efficient than using several VOC type-specific sensors or using a single sensitive instrument that could detect the respective concentration of each of several types of VOCs, such as a mass spectrometer. In various embodiments, sensors 110, 120, and 130 are sensors that operate independently of each other and therefore, generate three separate sensor data streams (e.g., each sensor data stream is its own time series) and each such sensor can be replaced without affecting the other two sensors on the same mobile sensor platform. In some embodiments, sensor 110, 120 and/or 130 may be a multi-modality sensor. A multi-modality gas sensor senses multiple gases or compounds. For example, if sensor 110 is a multi-modality $NO_2/O_3$ sensor, sensor 110 might sense both $NO_2$ and $O_3$ together.

Although not shown in FIG. 1, other sensors co-located with sensors 110, 120 and 130 may be used to sense characteristics of the surrounding environment including, in some instances, other gases, meteorological data, and/or particulate matter. Such additional sensors are exposed to the same environment as sensors 110, 120 and 130. In some embodiments, such additional sensors are in close proximity to sensors 110, 120 and 130, for example within ten millimeters or less. In some embodiments, the additional sensors may be further from sensors 110, 120 and 130 if the additional sensors sample the same packet of air inside of a closed system, such as a system of closed tubes. In some embodiments, temperature and/or pressure are sensed by these additional sensors. These additional co-located sensors may be used to calibrate sensors 110, 120 and/or 130. Although not shown, sensor platform 102A may also include a manifold for drawing in air and transporting air to sensors 110, 120 and 130 for testing.

Sensors 110, 120 and 130 provide sensor data over bus 106, or via another mechanism. In some embodiments, data from sensors 110, 120 and 130 incorporates time. This time may be provided by a master clock (not shown) and may take the form of a timestamp. The master clock may reside on sensor platform 102A, may be part of processing unit 140, or may be provided from server 150. As a result, sensors 110, 120 and 130 may provide timestamped sensor data to server 150. In other embodiments, the time associated with the sensor data may be provided in another manner. Because sensors 110, 120 and 130 generally capture data at a particular frequency, sensor data is discussed as being associated with a particular time interval (e.g., the period associated with the frequency), though the sensor data may be timestamped with a particular value. For example, sensors 110, 120 and/or 130 may capture sensor data every second, every two seconds, every ten seconds, or every thirty seconds. The time interval may be the same for all sensors 110, 120 and 130 or may differ for different sensors 110, 120 and 130. In some embodiments, the time interval for a sensor data point is centered on the timestamp. For example, if the time interval is one second and a timestamp is t1, then the time interval may be from t1−0.5 seconds to t1+0.5 seconds. However, other mechanisms for defining the time interval may be used.

Sensor platform 102A also includes a position unit 145 that provides position data. In some embodiments, position unit 145 is a global positioning satellite (GPS) unit. Consequently, system 100 is described in the context of a GPS unit 145. The position data may be time-stamped in a manner analogous to sensor data. Because position data is to be associated with sensor data, the position data may also be considered associated with time intervals, as described above. However, in some embodiments, position data (e.g., GPS data) may be captured more or less frequently than sensor data. For example, GPS unit 145 may capture position data every second, while sensor 130 may capture data every thirty seconds. Thus, multiple data points for the position data may be associated with a single thirty second time interval. The position data may be processed as described below.

Optional processing unit 140 may perform some processing and functions for data from sensor platform 104, may simply pass data from sensor platform 104 to server 150 or may be omitted.

Mobile sensors platforms 102B and 102C are analogous to mobile sensor platform 102A. In some embodiments, mobile sensor platforms 102B and 102C have the same components as mobile sensor platform 102A. However, in other embodiments, the components may differ. However, mobile sensor platforms 102A, 102B and 102C function in an analogous manner.

Server 150 includes sensor data database 152, processor(s) 154, memory 156 and position data database 158. Processor(s) 154 may include multiple cores. Processor(s) 154 may include one or more central processing units (CPUs), one or more graphical processing units (GPUs) and/or one or more other processing units. Memory 156 can include a first primary storage, typically a random-access memory (RAM), and a second primary storage area, typically a non-volatile storage such as solid-state drive (SSD) or hard disk drive (HDD). Memory 156 stores programming instructions and data for processes operating on processor(s) 154. Primary storage typically includes basic operating instructions, program code, data and objects used by processor(s) 154 to perform their functions. Primary storage devices (e.g., memory 156) may include any suitable computer-readable storage media, described below, depending on whether, for example, data access needs to be bi-directional or uni-directional.

Sensor data database 152 includes data received from mobile sensor platforms 102A, 102B and/or 102C. After capture by mobile sensor platform 102A, 102B and/or 102C, sensor data stored in sensor data database 152 may be operated on by various analytics, as described below. Position data database 158 stores position data received from mobile sensor platforms 102A, 102B and/or 102C. In some embodiments, sensor data database 152 stores position data as well as sensor data. In such embodiments, position data database 158 may be omitted. Server 150 may include other databases and/or store and utilize other data. For example, server 150 may include calibration data (not shown) used in calibrating sensors 110, 120 and 130.

System 100 may be used to capture, analyze, and provide information regarding hyper-local environmental data. Mobile sensor platforms 102A, 102B, and 102C may be used to traverse routes and provide sensor and position data to server 150. Server 150 may process the sensor data and position data. Server 150 may also assign the sensor data to map features corresponding to the locations of mobile sensor platforms 102A, 102B, and 102C within the same time interval as the sensor data was captured. As discussed above, these map features may be hyper-local (e.g., one hundred meter or less road segments or thirty meter or less road segments). Thus, mobile sensor platforms 102A, 102B, and 102C may provide sensor data that can capture variations on this hyper-local distance scale. Server 150 may provide the environmental data, a score, confidence score and/or other assessment of the environmental data to a user. Thus, using system 100 hyper-local environmental data may be obtained using a relatively sparse network of mobile sensor platforms 102A, 102B, and 102C, associated with hyper-local map features and processed for improved understanding of users.

Figure 2:
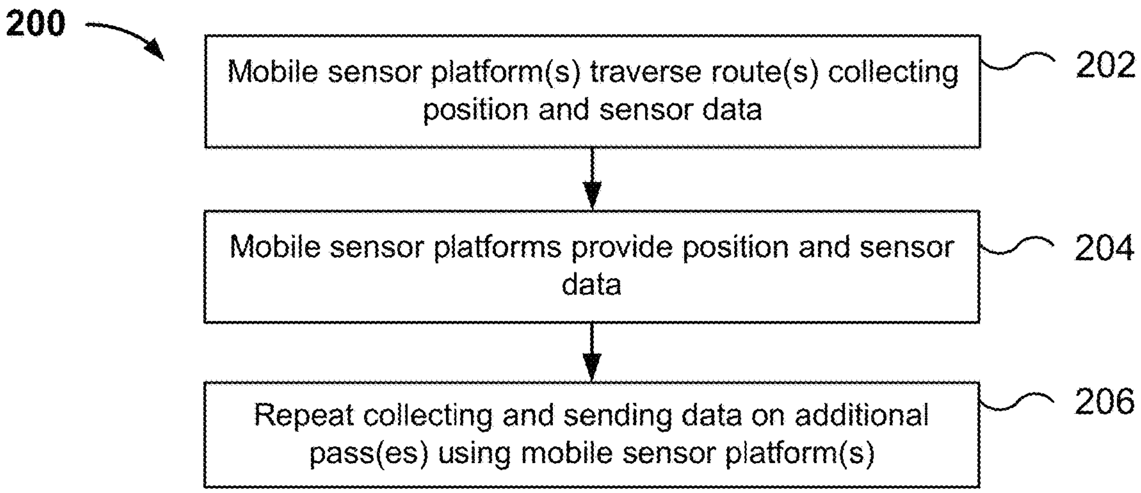
FIG. 2 depicts an exemplary embodiment of method 200 for capturing environmental data using mobile sensor platforms, such as mobile sensor platforms 102A, 102B and/or 102C and server 150.

FIG. 2 depicts an exemplary embodiment of method 200 for capturing environmental data using mobile sensor platforms, such as mobile sensor platforms 102A, 102B and/or 102C and server 150. Method 200 is described in the context of system 100, but may be performed using other systems. For clarity, only some portions of method 200 are shown. Although shown in a sequence, in some embodiments, processes may occur in parallel and/or in a different order.

Mobile sensor platforms traverse routes in a geographic area, at 202. While traversing the routes, the mobile sensor platforms collect not only sensor data, but also position data. For example, a mobile sensor platform may sense one or more of $NO_2$, CO, NO, $O_3$, $SO_2$, $CO_2$, $CH_4$, $C_2H_6$, VOCs, particulate matter in one or more size ranges, other compounds, radiation, noise, light and other environmental data at various times during traversal of the route. Other environmental characteristics, including but not limited to temperature, pressure, and/or humidity may also be sensed at 202. In addition, the time corresponding to the environmental data is also captured. The time may be in the form of a timestamp for the sensor data (sensor timestamp), which may correspond to a particular time interval. Different sensors on the mobile sensor platform may capture the environmental data at different times and/or at different frequencies. Also at 202, the mobile sensor platforms capture position data, for example via a GPS unit. The position data may include location (as indicated by a GPS unit), velocity and/or other information related to the geographic location of the mobile sensor platform. In some embodiments, position data from other sources, such as acceleration, may be captured from the vehicle or another source. The position data may include a timestamp (position timestamp) or other indicator of the time at which the position data is captured.

The mobile sensor platforms provide the position and sensor data to a server, at 204. In some embodiments, mobile sensor platforms provide this data substantially in real-time, as the mobile sensor platforms traverse their routes at 202. Thus, the position and sensor data may be transmitted wirelessly to the server. In some embodiments, some or all of the position and/or sensor data is stored at the mobile sensor platform and provided to the server at a later time. For example, the data may be transferred to the server when the mobile sensor platform returns to its base. In some embodiments, the mobile sensor platform may process the sensor data and/or position data prior to sending the sensor and/or position data to the server. In other embodiments, the mobile sensor platform provides little or no processing. The sensor data and position data may be sent at the same time or may be sent separately.

At 206, the route traversal and data collecting of 202 and data sending of 204 are repeated. Thus, the mobile sensor platforms may traverse the same or different routes at 206. In either case, multiple passes of the same geographic locations, and thus multiple passes of the same corresponding map features, are made at 206. In some embodiments, the repetition at 206 may be periodic (e.g., approximately every week, month or other time period). In some embodiments, the repetition at 206 may be performed based on other timing. In some cases, the same mobile sensor platform is sent on the same route and/or collects data for the same map features. In some embodiments, different mobile sensor platforms collect data that may be used for the same routes and/or map features. Also at 206, steps 202 and 204 may be performed multiple times. Thus, at 206, data for a particular region may be aggregated over time.

Figure 3A:
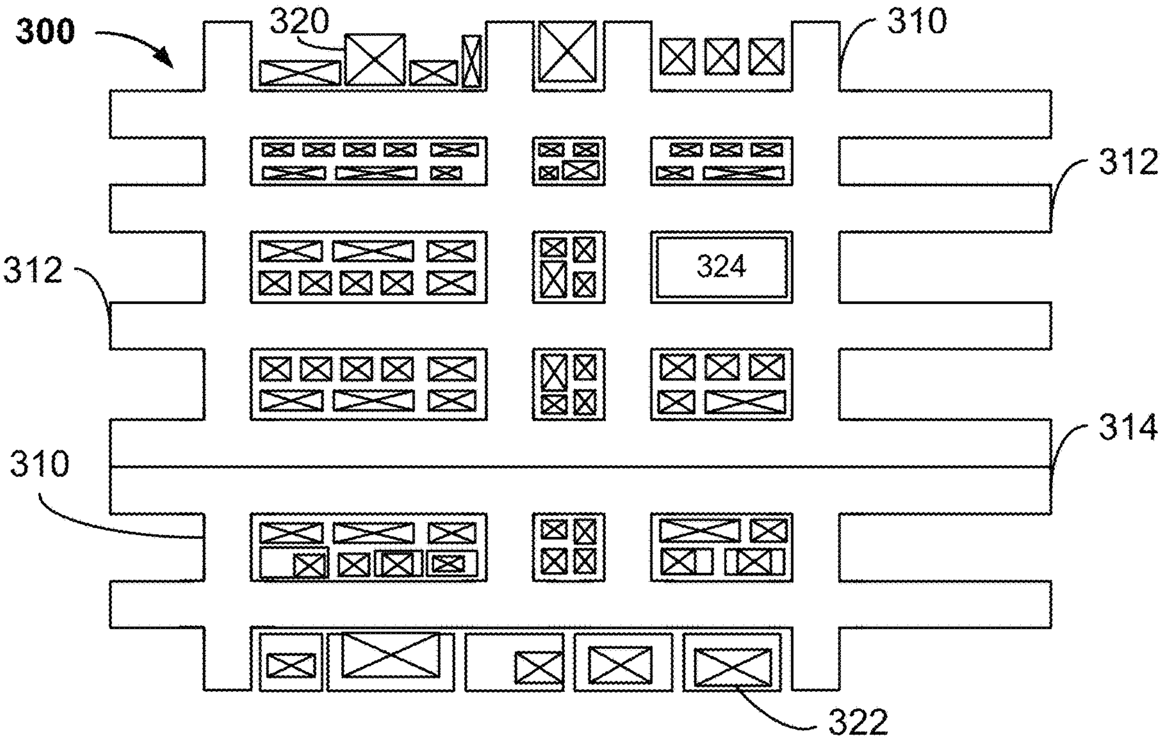
FIGS. 3A-3C illustrate a particular geographic area and the routes that may be traversed using method 200.
Figure 3B:
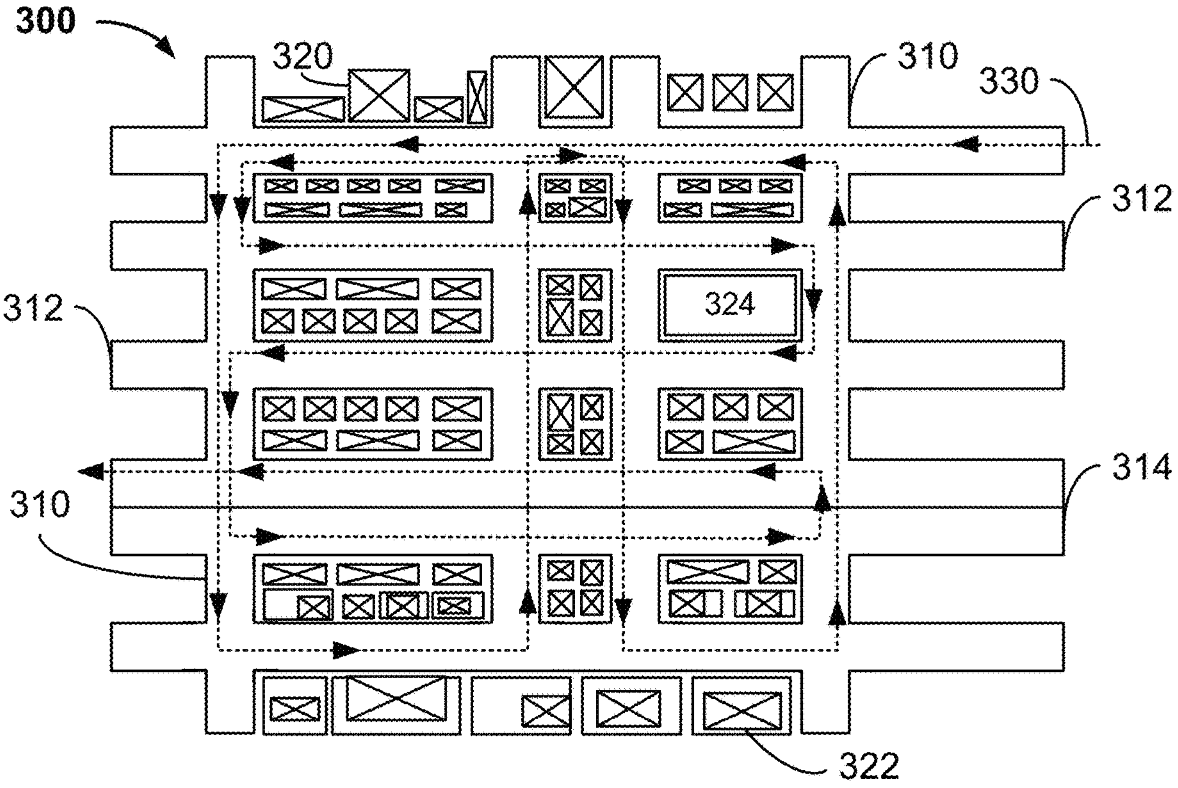
Figure 3C:
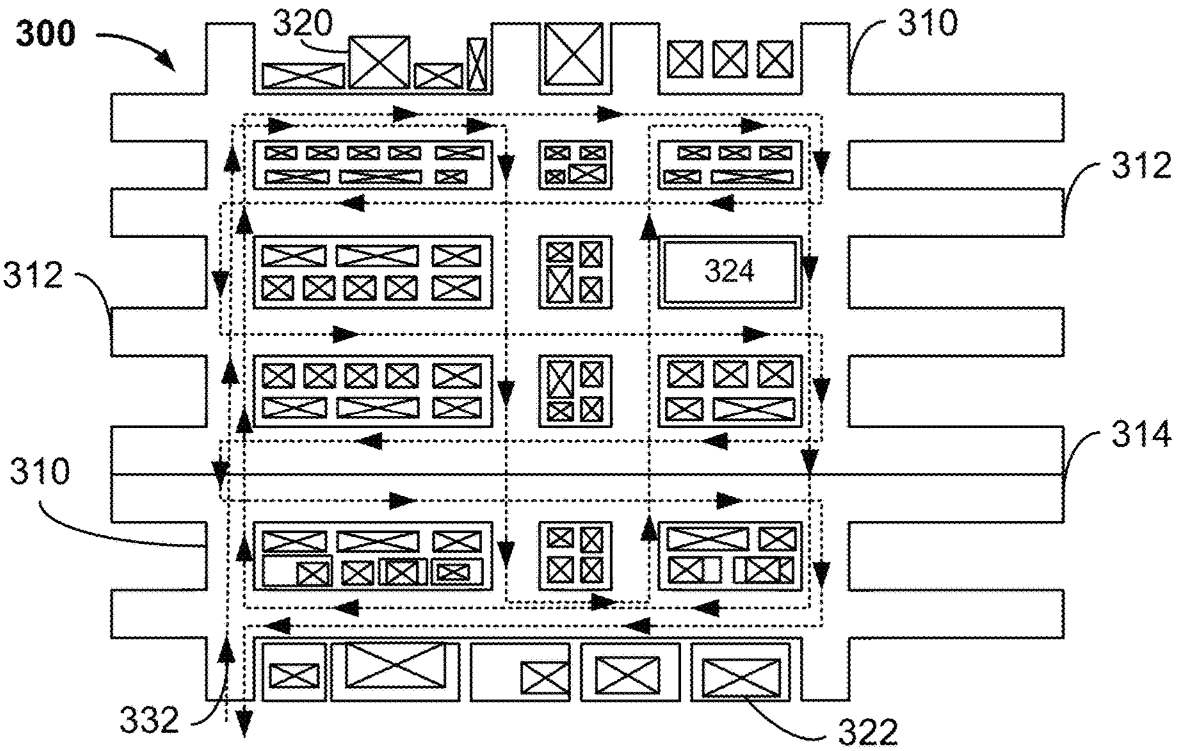

For example, FIGS. 3A-3C illustrate a particular geographic area and the routes that may be traversed using method 200. A map 300 corresponding to the geographic area is shown in FIG. 3A. Map 300 may be an open-source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot or analogous item. As can be seen in FIG. 3A, the density and size of structures 320 and 322 vary across map 300. Similarly, the density and size of streets 310, 312 and 314 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by GPS unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation, and analysis. Sensor data and position data are sensed sufficiently frequently using method 200 that variations in environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

The sensor data captured and provided to server 150 is further processed. For example, data from multiple runs of mobile sensor platforms, such as mobile sensor platform 104, and stationary sensor data may be aggregated. In particular, data for locations (e.g., each road segment) captured on multiple runs at different times may be aggregated, additional processing performed, and statistical values such as the mean, average, and percentiles, calculated. Other processing may include background correction. For example, background values for particulate matter may be measured on days with rain or a specified portion of the lowest part of the distribution (e.g., the lowest ten percent or twenty percent) may be identified as the background. This background may then be subtracted from the distribution. Other techniques for accounting for the background may be used in other embodiments. In some embodiments, the background may be determined in different ways for different geographic regions (e.g., based on neighborhoods, cities or counties). In some embodiments, the background may be accounted for at only some locations.

Thus, using method 200 and system 100, environmental data may be sensed at hyperlocal scales and analyzed. In various embodiments, VOC sensor data as well as non-VOC sensor data are collected at hyperlocal scales and analyzed using method 200 and system 100. In some embodiments, each mobile sensor platform (e.g., 102A of system 100) includes at least one TVOC sensor and a set of non-VOC sensors (sensors that are configured to respectively detect different types of pollutants other than VOCs). Different specific types of VOC pollutants (e.g., benzene, ethylbenzene, toluene, or xylene) may be associated with different types of sources. However, while the TVOC sensor does not indicate which specific VOC type pollutants are detected but only the collective amount of VOCs detected, it is advantageous to equip a mobile sensor platform with TVOCs because the cost of a single TVOC is less than the cumulative costs of various VOC type-specific sensors and also less than a single sensitive instrument that can detect the respective amounts of various specific VOC type pollutants. TVOC sensors are also beneficial in that a single TVOC sensor would occupy less volume/space per each mobile sensor platform than the alternative of multiple VOC type specific sensors or a single sensitive instrument that can detect the respective amounts of various specific VOC type pollutants. To analyze the VOC sensor data streams that are collected from TVOC sensors, peaks are first identified within the VOC sensor data streams and the non-VOC sensor data streams. Then, the VOC peaks are correlated with the non-VOC peaks to classify the source types of the VOC peaks, as will be described in further detail below. As such, the non-VOC sensor data can be leveraged to infer the source type classification of each VOC peak even if the measured TVOC data does not identify the specific VOC pollutants that make up the measurements.

Figure 4:
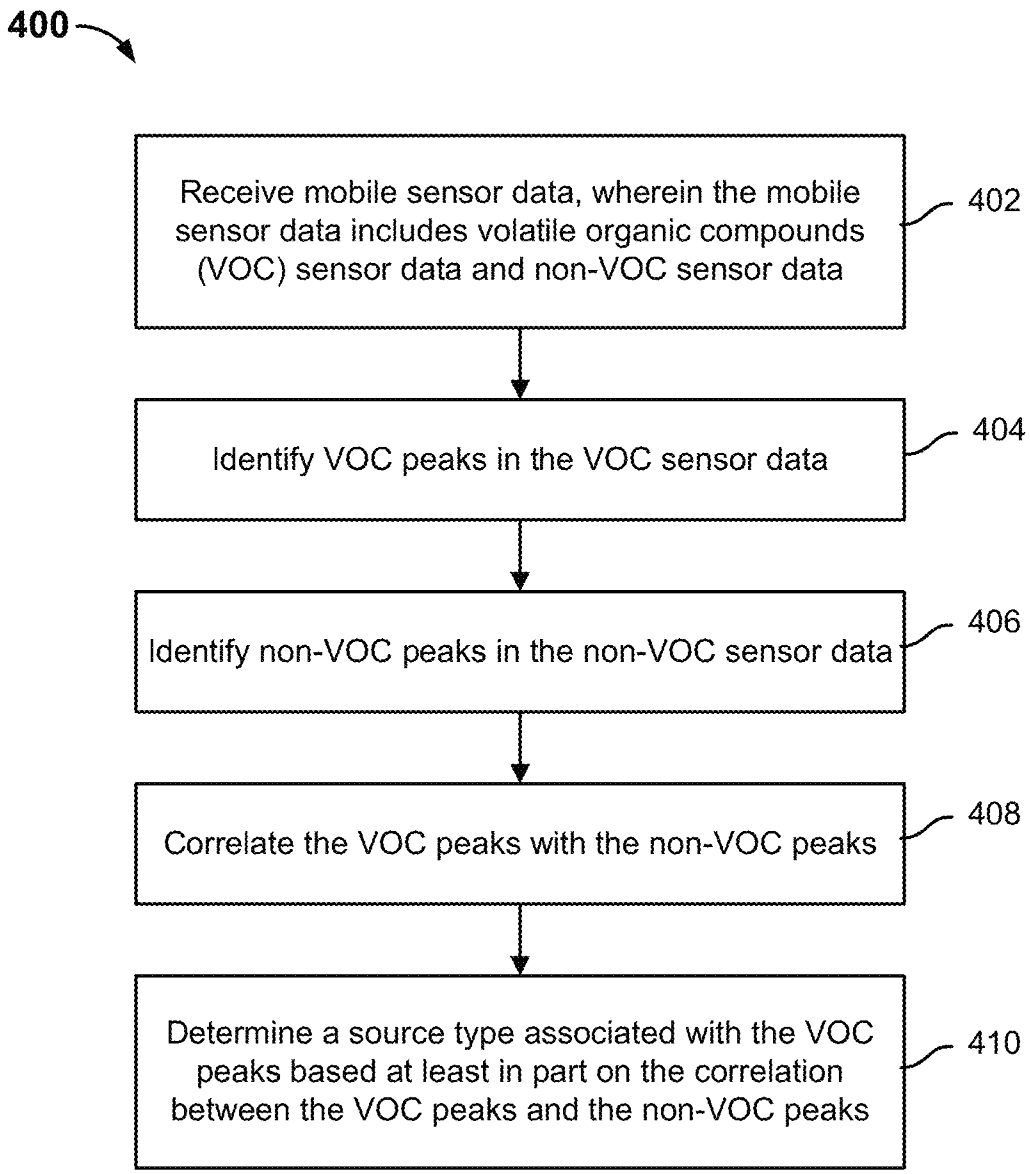
FIG. 4 depicts an exemplary embodiment of method 400 for the detection of volatile organic compounds.

FIG. 4 depicts an exemplary embodiment of method 400 for the detection of volatile organic compounds. Method 400 is described in the context of system 100 of FIG. 1, but may be performed using other systems. Specifically, as described below, method 400 may be carried out on multiple sensor systems, such as mobile sensor systems 102A, 102B and 102C and server 150. For clarity, only some portions of method 400 are shown. Although shown in a sequence, in some embodiments, processes may occur in parallel and/or in a different order (including in parallel).

At 402, mobile sensor data is received, wherein the mobile sensor data includes volatile organic compounds sensor data and non-VOC sensor data. In various embodiments, the mobile sensor data is received from sensors that are part of mobile sensor platforms (e.g., mobile sensors platforms 102A, 102B, and 102C of system 100). As described above in method 200, mobile sensor platforms repeatedly traverse routes within a geographic area, while collecting sensor data that corresponds to time and location data. The mobile sensor platforms each includes a set of sensors, which comprises a sensor that detects VOC amounts (e.g., a TVOC sensor) and one or more sensors that detect non-VOC pollutants (e.g., $NO_2$, CO, NO, $O_3$, $SO_2$, $CO_2$, $CH_4$, and/or $C_2H_6$,). In some embodiments, the sensor that detects VOCs is independent from the sensor(s) that detect non-VOC data and therefore, the VOC sensor data and the non-VOC sensor data are independent data streams.

Sensor data are accrued while the mobile sensor platforms are in motion, at step 402. Thus, VOCs and other constituents of the air are sampled. At step 402, at least some of the VOCs and other measurements are made while the vehicle is in motion. In some embodiments, total VOCs are measured at step 402. In some embodiments, data are sampled at a frequency of at least 0.5 Hz and not more than 4 Hz. In some embodiments, data are sampled at 1 Hz. Other sampling frequencies are possible. In some embodiments, additional and/or other substances may also be detected at step 402. Further, data are passively sampled at step 402. In some embodiments, therefore, the data may simply be collected without user intervention. For example, data are collected as the vehicle travels over a region and/or while in motion. Stops by the driver may be made for other reasons (e.g., stop signs, traffic signals, etc.). Thus, the data may be passively captured during routine vehicle operation by individuals, as fleet vehicles or as part of a network of vehicles (e.g., vehicles that are distributed and may be independently as opposed to centrally operated, but which may be in communication with each other or with a central system).

In some embodiments, the route taken by one or more vehicles at step 402 is selected based on various criteria. For example, a route may be selected to evenly cover an area or to focus on regions at which VOCs are more likely to occur. The route may be updated during operation of the vehicle. For example, in response to regions in which the VOCs detected is high, part of the route may be re-traversed. In some embodiments, there may be no route specified for the purposes of data collection. Instead, data is collected as the vehicle travels through the routes selected by the operator. For example, the sensor system may be mounted in a private individual's vehicle and data collected as the private individual travels in the vehicle to carry out their own tasks. In addition to total VOCs (e.g., VOCs including but not limited to BTEXs), other data may be collected as part of step 402. For example, the time each sample is taken (i.e., a time stamp) and the location of each sample can be measured and recorded. Further, data for other environmental constituents (e.g., methane, ethane, NO, $NO_2$, PM2.5, black carbon, ozone, CO, and/or $CO_2$) may be similarly captured. In some embodiments, step 402 includes sending the sensor data from the mobile sensor platform to a centralized or other data processing system. In some embodiments, step 402 implements some or all of method 200.

At 404, VOC peaks are identified in the VOC sensor data.

At 406, non-VOC peaks are identified in the non-VOC sensor data.

At 408, the VOC peaks are correlated with the non-VOC peaks.

The data are processed at steps 404, 406 and 408. In some embodiments, steps 404, 406 and 408 are performed asynchronously with 402. For example, one or more mobile sensor platforms such as systems 102A, may collect and transmit data to a centralized system 150 for processing as part of 402.

After some or all of the data is received at the processing system, steps 404, 406 and 408 are performed. VOC peaks (if any) are identified from the VOC sensor data, at step 404. In various embodiments, any event detection methods via signal processing could be used to detect VOC peaks among VOC sensor data. For example, identification of peaks includes determining whether the amount of the corresponding pollutant exceeds a threshold for that pollutant. In various embodiments, when the received mobile sensor data includes a time series of pollutant concentration, then a peak is a portion (e.g., a subset of data points/samples) within the time series in which the pollutant concentration exceeds a threshold. In some embodiments, the threshold for the pollutant is based on a rolling baseline. The rolling baseline is the median of the measurements of the pollutant for a given time window/temporal neighborhood (e.g., thirty seconds, a minute, two minutes, or four minutes) around the time the sample(s) were captured. In some embodiments, the threshold may be selected to be at least the baseline. Lower thresholds generally have a higher sensitivity to the pollutant being detected and may result in more peaks being identified. In some embodiments, the threshold may be selected based upon the noise in the sensor(s) that sample VOCs. For example, in various embodiments, sensor data has a threshold of at least two multiplied by the sensor noise floor, three multiplied by the sensor noise floor, four multiplied by the sensor noise floor, five multiplied by the sensor noise floor, six multiplied by the sensor noise floor, ten multiplied by the sensor noise threshold, twelve multiplied by the sensor noise floor, or a greater multiple of the sensor noise floor. Data exceeding the corresponding threshold may be counted as an accurate measurement of a significant enhancement in VOCs.

The identified VOC peaks identified are associated with a location. For example, if a VOC peak were associated with multiple data points in the sensor data stream, then the location associated with the VOC peak could be the center of the recorded location data associated with those data points. The location associated with a VOC peak can be any spatial unit such as, for example, a particular road segment, particular latitude/longitude coordinates, and/or a particular grid cell (e.g., a hexbin (a hexagonal grid cell), or other shape of which the road segments on which data are accrued are part of). The VOC peaks may thus be considered to be identified as peaks, geolocated (e.g., to a road segment, to latitude/longitude coordinates, to a hexbin, or to another location) and timestamped. The timestamp corresponds to the time at which the data is collected. For example, if a VOC peak were associated with multiple data points in the sensor data stream, then the location associated with the VOC peak could be the average of the recorded timestamps associated with those data points.

Non-VOC peaks can be determined from non-VOC sensor data in step 406 analogously to how VOC peaks are determined in step 406. For example, each non-VOC peak can be determined as a portion of a time series of non-VOC pollutant data points with pollutant concentration that exceeds a threshold and where the threshold is determined as a function of a rolling baseline.

It is also determined whether the VOC peaks and the non-VOC peaks are correlated, at step 408. Peaks being correlated include at least one of a correlation in peak shape, peaks being temporally co-located (e.g., having data time stamped within a particular interval), peaks being geographically co-located (e.g., the locations being correlated as occurring within a particular distance), and/or peaks having the appropriate ratio for a particular type of constituents. For example, the particular interval over which peaks can be determined to be temporally co-located can be peak dependent. For instance, imagine a plume through which a vehicle with a mounted mobile sensor system is driving. Other peaks could be identified within the plume as correlated, and then the sensors' time within the plume via the peak's shape is determined. Then, correlation can be expressed as a time interval based on that time-in-plume. For example, the locations of these peaks may be correlated (e.g., considered to be at the same location/be co-located) if determined to be within a threshold distance, such as, for example, less than thirty meters, of each other. In some embodiments, the locations of the peaks may be determined and correlated to within ten meters. In some embodiments, the locations of the peaks may be determined and correlated to within six meters. Temporal correlations may be determined in an analogous manner. For example, the time of the peaks may be determined and correlated to within 24 hours. Thus, there may be a difference in the time that VOC peaks and/or other components of the atmosphere (e.g., non-VOC peaks) are detected even if they are from the same source. Thus, data for VOC peaks and/or other environmental components (e.g., non-VOC peaks) may be time shifted as part of correlating the peaks in step 408 and/or determining the existence of peaks at steps 404 and 406. This time shifting may relate to the instrument response time and to the residence time of the air sample in a manifold that routes air samples to the sensors.

As part of the correlation determined at step 408, statistics on the VOC peaks and correlated non-VOC peaks from other sensed components of the atmosphere are collected. This data may be used in conjunction with other data that is collected. For example, the peak-to-pass ratio (e.g., the number of times a peak is detected at a location divided by the number of times data is collected by a mobile sensor platform for the location while driving a distinct route), the number of distinct dates for which a peak is found at a location, and/or whether there are three (or some other number greater than one) separate indicators of the peak being present within twenty-five meters (or some other distance) of the location may be determined using the analyzed VOC data. Of these, the separate indicators of the peak may be determined at 408 from a dataset for a single route.

At 410, a source type associated with the VOC peaks are determined based at least in part on the correlation between the VOC peaks and the non-VOC peaks.

The source type of each VOC peak is determined based on that VOC peak's correlation (or lack thereof) with non-VOC peaks at step 408. In various embodiments, the "source type" of a VOC peak is a classification/category of the type of source from which the VOCs in the VOC peak may have originated. In various embodiments, any number of source types may be configured. Some specific examples of source types include a combustion source type (where VOCs were emitted from a source of a combustive/burning event), a non-combustion VOC source type (where VOCs were emitted from a non-combustive/burning event), and a third VOC (e.g., only) source type (where VOCs were emitted from a source that is neither combustive or non-combustive but evaporative). For example, if no non-VOC peak is co-located with a VOC peak (i.e., the peak(s) for a location or region are VOC only), the source type of the VOC peak may be VOC only (which is sometimes herein referred as a "TVOC" source type). Examples of a VOC only (TVOC) source type may include an evaporative source such as a gas station, leaking fuel tank, or nail salon. If CO, $CO_2$, and/or NO types of combustive but non-VOC peaks are co-located with the VOC peak, the source type may be a combustion source type (which is sometimes herein referred as a "combustion" source type). Examples of a combustion source type may include moving traffic or another location that burns fuel. If non-combustive types of non-VOC peaks are co-located with the VOC peak, the source type may be a non-combustion source type (which is sometimes herein referred to as a "TVOC+" source type). An example of a TVOC+ source type may include cooking emissions from a restaurant. The locations of VOC peaks of the combustion, non-combustion, and other source types may be in proximity to the actual locations from which they were emitted. For example, the VOC peaks associated with combustion sources (which are primarily from on-road mobile emissions) may be ignored if only stationary sources of VOCs are of primary interest. A VOC peak's source type classification may be determined based on correlations (or not) with non-VOC peaks, as described herein, and/or using decision tree(s) and probabilistic models.

For example, one or more of mobile sensor systems 102 are used to passively sample the environment in a moving vehicle at step 402. Sensor systems 102 thus capture total VOC sensor data over the route(s) driven. Other data, such as NO, CO, $CO_2$, PM2.5, methane, ethane, and/or other constituents of the environment may also be captured by the sensor systems 102 over the same route(s) by the same sensor systems 102. The data collected by system(s) 102 may be uploaded to server 150 for processing at steps 404, 406, 408 and 410. This upload may take place remotely (e.g., while the vehicle carrying sensor system 102 is driven) or while the vehicle is in proximity to server 150. VOC and other non-VOC sensor data are processed. Thus, for each route driven (e.g., each series of time stamped data collected), the VOCs are detected and corresponding peaks are identified. Similar processing may take place for other non-VOC measurements. VOC and other peaks may be correlated for the route. Based on the data captured, as well as other information such as wind speed; maps indicating the locations of gas stations and/or other VOC sources; and topographical maps, the location of the source may also be determined for the data sensed at 402.

Using method 400, VOC peaks may be detected and ultimately classified into a source type. The method may be extended to be used with a number of systems, such as systems 102A, 102B and 102C and/or server 150. Peaks from different sensor systems 102 mounted on different vehicles may be used to detect VOC peaks using method 400. Method 400 may also be repeated over time internals using one or more systems. Thus, the VOCs, peaks in VOCs, emission source type (e.g., combustion, non-combustion, and/or other), and/or possible sources may be determined. Method 400 may be repeated multiple times using the same or different mobile sensing systems simultaneously and at different times. Repeating method 400 over the course of a specified time period (e.g., over a month, a quarter, a year, and/or multiple years) may provide temporal information about when, where, and how many VOC peaks are detected over the specified time period.

Figure 5:
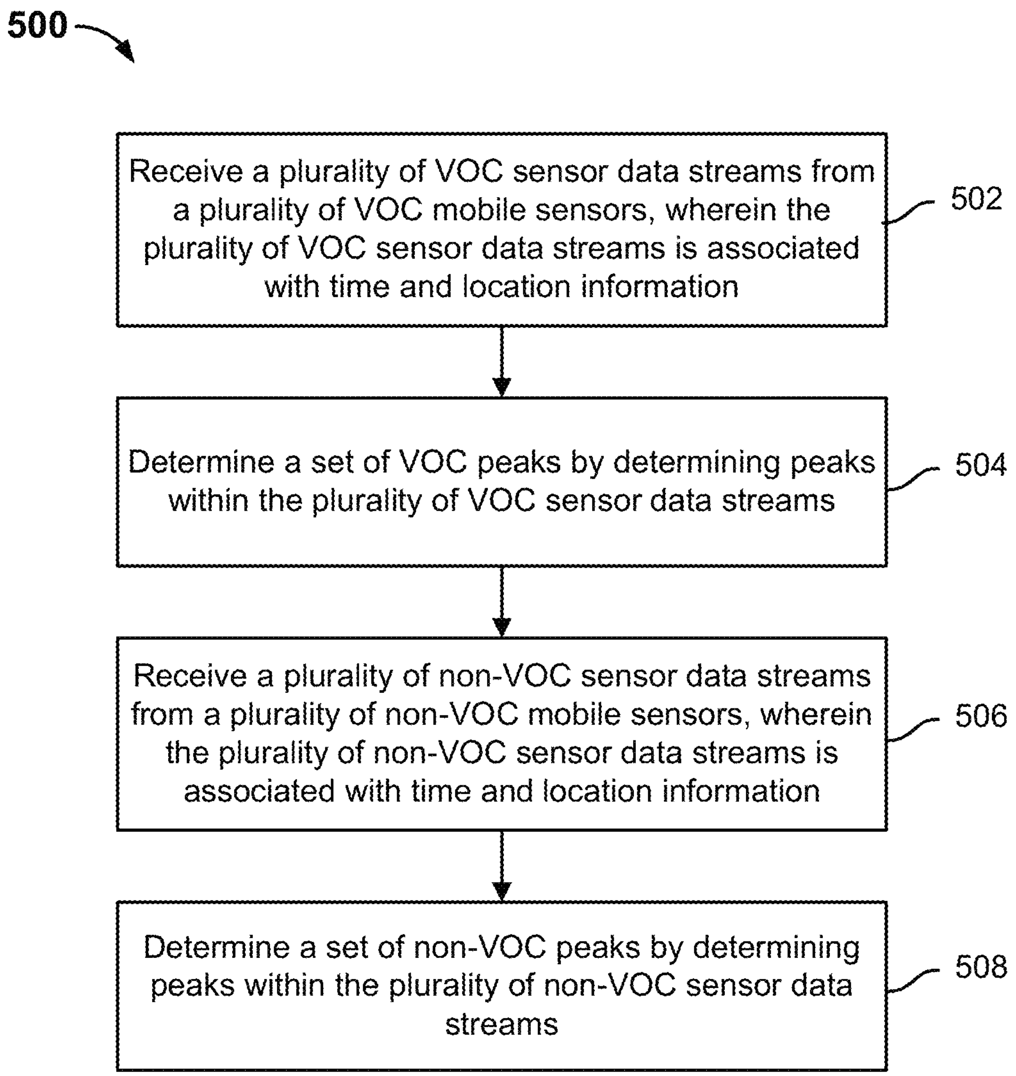
FIG. 5 depicts an exemplary embodiment of method 500 for the detection of peaks within sensor data streams.

FIG. 5 depicts an exemplary embodiment of method 500 for the detection of peaks within sensor data streams. Method 500 is described in the context of system 100 of FIG. 1, but may be performed using other systems. Specifically, as described below, method 500 may be carried out on multiple sensor systems, such as mobile sensor systems 102A, 102B and 102C and server 150. For clarity, only some portions of method 500 are shown. Although shown in a sequence, in some embodiments, processes may occur in parallel and/or in a different order (including in parallel). In some embodiments, steps 402, 404, and 406 of process 400 of FIG. 4 may be implemented, at least in part, using process 500.

At 502, a plurality of VOC sensor data streams is received from a plurality of VOC mobile sensors, wherein the plurality of VOC sensor data streams is associated with time and location information. In some embodiments, the VOC (e.g., TVOC) sensor data streams were received from VOC (e.g., TVOC) sensors that were part of mobile sensor platforms. In some embodiments, each VOC sensor data stream is a time series of VOC measurements/data points and where each data point (e.g., measured TVOC concentration) is associated with a corresponding location (e.g., GPS coordinate) and timestamp.

At 504, a set of VOC peaks is determined by determining peaks within the plurality of VOC sensor data streams. In various embodiments, VOC peaks can be determined from VOC sensor data streams using any event detection methods via signal processing. In some embodiments, a sliding window is applied to each VOC data (e.g., measured concentration) time series to determine whether a VOC peak is present within that window. In some embodiments, a VOC peak is determined within a sliding window (e.g., that is thirty seconds, a minute, two minutes, or four minutes in width) if the measured VOC sensor data exceeds a threshold and where, for example, the threshold is determined as a function (e.g., multiple) of a predetermined value and the rolling VOC sensor baseline within the sliding window. The rolling baseline is the median of the measurements of the VOC sensor data within the sliding window. Put another way, a VOC peak is determined as a peak in measured VOC (e.g., TVOC) concentration within a temporal neighborhood. A VOC peak is associated with a corresponding location (e.g., which is determined as the center of the location information associated with the VOC data point(s) that are included in the VOC peak) and a corresponding time (e.g., which is determined as the average of the timestamps associated with the VOC data point(s) that are included in the VOC peak.

At 506, a plurality of non-VOC sensor data streams is received from a plurality of non-VOC mobile sensors, wherein the plurality of non-VOC sensor data streams is associated with time and location information. In some embodiments, the non-VOC sensor data streams were received from different non-VOC types of sensors (e.g., methane, ethane, NO, $NO_2$, PM2.5, black carbon, ozone, CO, and/or $CO_2$) that were part of mobile sensor platforms. In some embodiments, each non-VOC sensor data stream is a time series of non-VOC measurements/data points and where each data point (e.g., measured TVOC concentration) is associated with a corresponding location (e.g., GPS coordinate) and timestamp.

At 508, a set of non-VOC peaks is determined by determining peaks within the plurality of non-VOC sensor data streams. In some embodiments, non-VOC peaks can be determined analogously to how VOC peaks are determined at step 504.

Figure 6:
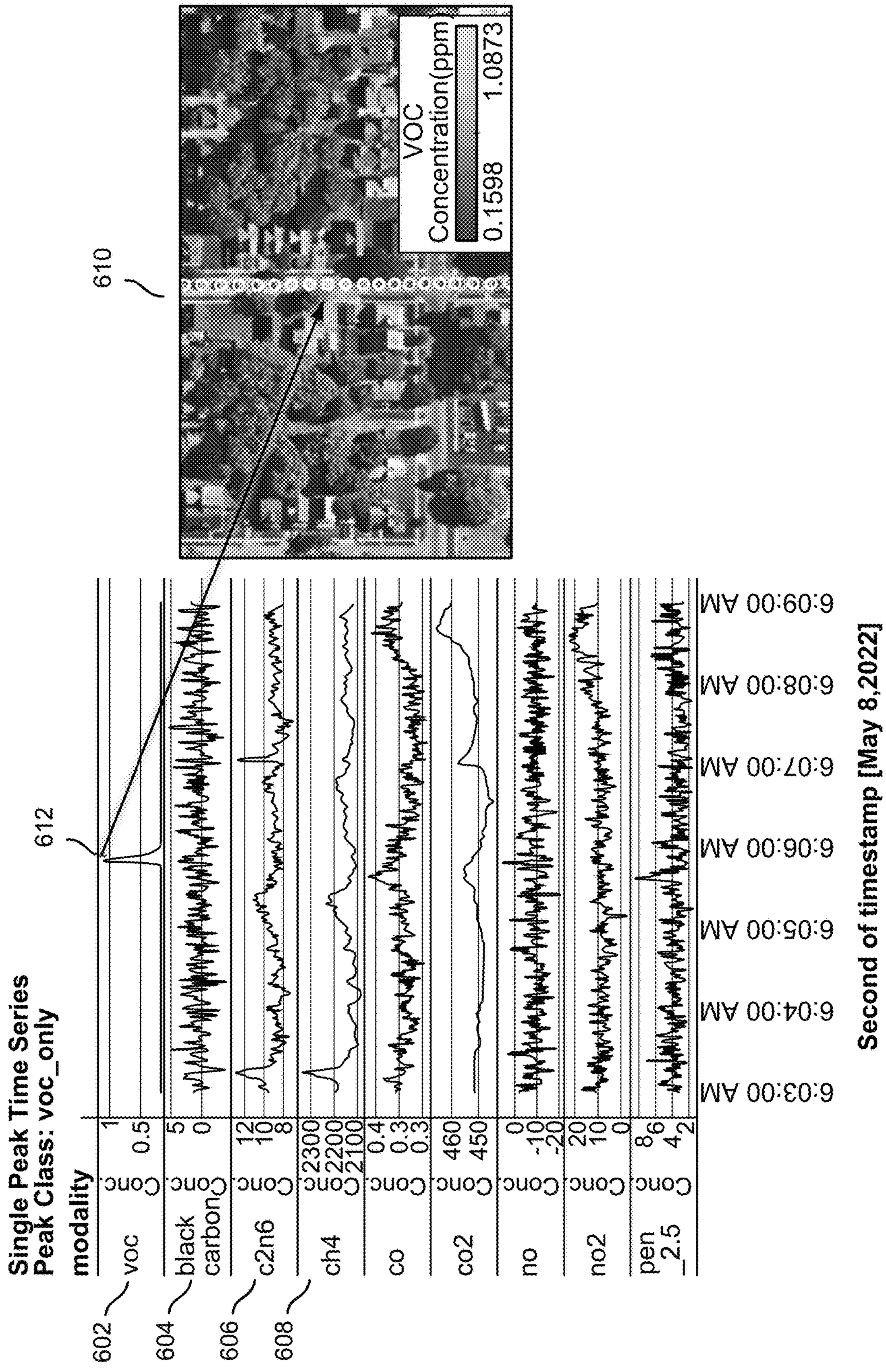
FIG. 6 is a diagram that shows respective data streams for VOC sensor data and various non-VOC sensor data.

FIG. 6 is a diagram that shows respective data streams for VOC sensor data and various non-VOC sensor data. In particular, FIG. 6 shows the detailed temporally and spatially resolved concentrations of VOCs and other non-VOC pollutants. Time series 602 shows the measured data points (concentrations) of VOC (e.g., TVOC) across time. The same measured data VOC data points of time series 602 are also shown at their corresponding recorded locations along a segment of a road as shown in birds-eye view of the road in image 610. VOC peak 612, which is associated with a high VOC concentration within its temporal neighborhood, is also detected within time series 602 and its corresponding location along the road shown in image 610 is also identified. FIG. 6 also shows time series 604, 604, 606, and 608 (among others) that respectively show the measured data points (concentrations) of non-VOC pollutants such as black carbon, $C_2N_6$, $CH_4$, CO, and $CO_2$ across time. Non-VOC peaks can be also similarly identified across each of time series 604, 604, 606, and 608. As shown in FIG. 6, time series 604, 604, 606, and 608 of measured non-VOC data points are time-aligned and space-aligned with time series 602 of measured VOC data points. In the specific of FIG. 6, VOC peak 612 does not correlate either temporally or spatially with any on non-VOC peaks within time series such as 604, 604, 606, and 608 and is therefore determined to be a source type associated with VOC only (which is sometimes herein referred to as "TVOC").

Figure 7:
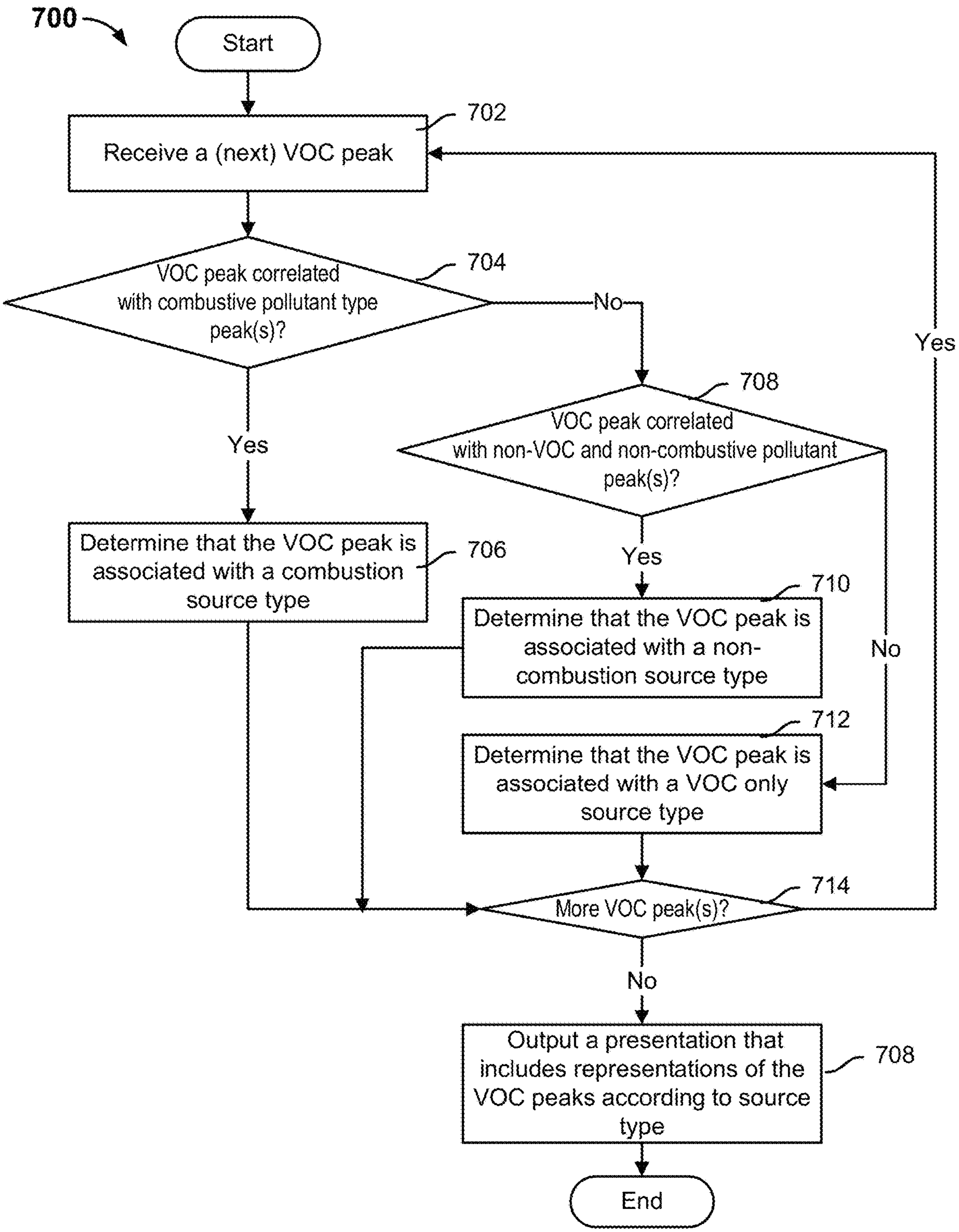
FIG. 7 depicts an exemplary embodiment of method 700 for the determining of a source type for a VOC peak based on the VOC peak's correlation(s) with other non-VOC peak(s).

FIG. 7 depicts an exemplary embodiment of method 700 for the determining of a source type for a VOC peak based on the VOC peak's correlation(s) with other non-VOC peak(s). Method 700 is described in the context of system 100 of FIG. 1, but may be performed using other systems. Specifically, as described below, method 700 may be carried out on multiple sensor systems, such as mobile sensor systems 102A, 102B and 102C and server 150. For clarity, only some portions of method 700 are shown. Although shown in a sequence, in some embodiments, processes may occur in parallel and/or in a different order (including in parallel). In some embodiments, steps 408 and 410 of process 400 of FIG. 4 may be implemented, at least in part, using process 700.

At 702, a (next) VOC peak is received. As described above, VOC peaks are detected among mobile sensor data (e.g., using a process such as process 500 of FIG. 5). Each VOC peak is associated with time and location information. As described above, the VOC peak is to be correlated with non-VOC peaks along one or more attributes of: time, location/space, peak shape, and peak-to-pass ratio. For example, the locations of a VOC peak and a non-VOC peak may be correlated (e.g., considered to be at the same location/be co-located) if determined to be within a threshold distance, such as, for example, less than thirty meters, of each other. In some embodiments, the locations of the peaks may be determined and correlated to within ten meters. In some embodiments, the locations of a VOC peak and a non-VOC peak may be determined and correlated to within six meters. Temporal correlations may be determined in an analogous manner. For example, the time of the peaks may be determined and correlated to within 24 hours. Thus, there may be a difference in the time that a VOC peak and a non-VOC peak are detected even if they are from the same source. Thus, data for a VOC peak and a non-VOC peak) may be time shifted as part of correlating the peaks in step 408 and/or determining the existence of peaks. This time shifting may relate to the instrument response time and to the residence time of the air sample in a manifold that routes air samples to the sensors.

At 704, whether the VOC peak is correlated with combustive pollutant type peak(s) is determined. In the event that the VOC peak is correlated with combustive pollutant type peak(s), control is transferred to 706. Otherwise, in the event that the VOC peak is not correlated with combustive non-VOC pollutant type peak(s), control is transferred to 708. In particular, at step 704, the VOC peak in question is compared with non-VOC peaks associated with pollutants that are associated with combustions. Examples of such combustive pollutants include CO, $CO_2$, and NO.

At 706, it is determined that the VOC peak is associated with a combustion source type. If the VOC peak is correlated (e.g., within a given margin/threshold) along one or more attributes with any one or more combustive non-VOC pollutant (e.g., CO, $CO_2$, and/or NO) peaks, then the VOC peak is classified to be of a combustion source type (e.g., this source type is sometimes referred to as the "Combustion" source type), meaning that the VOC peak is potentially emitted from a source that is of a combustion (e.g., burning) nature (e.g., from car engines).

At 708, whether the VOC peak is correlated with non-combustive pollutant type peak(s) is determined. In the event that the VOC peak is correlated with non-combustive pollutant type peak(s), control is transferred to 710. Otherwise, in the event that the VOC peak is not correlated with non-combustive non-VOC pollutant type peak(s), control is transferred to 712. At step 708, the VOC peak in question is compared with non-VOC peaks associated with pollutants that are not associated with combustions. Examples of such non-combustive pollutants include methane ($CH_4$) and fine particulate matter (PM2.5).

At 710, it is determined that the VOC peak is associated with a non-combustive source type. If the VOC peak is correlated (e.g., within a given margin/threshold) along one or more attributes with any one or more non-combustive non-VOC pollutant peaks, then the VOC peak is classified to be of a non-combustive source type that is nevertheless still associated with other pollutants (e.g., this source type is sometimes referred to as the "TVOC+" source type), meaning that the VOC peak is potentially emitted from a source that is not related to a burning nature. An example of a TVOC+ source is a cooking process/restaurant.

At 712, it is determined that the VOC peak is associated with a VOC only source type. If the VOC peak is not correlated (e.g., within a given margin/threshold) along one or more attributes with any one or more other non-VOC peaks associated with either combustive or non-combustive pollutants, then the VOC peak is classified to be of a VOC-only source type (e.g., this source type is sometimes referred to as the "TVOC" source type), meaning that the VOC peak is potentially emitted from not a combustive but rather to an evaporative nature (e.g., a business the provides dry cleaning or nail painting services). Examples of TVOC source types includes a fuel leak, a nail salon, or a gas station.

At 714, whether there is at least one more VOC peak for which a source type is to be determined. In the event there is at least one more VOC peak for which a source type is to be determined, control is returned to 702. Otherwise, there are no more VOC peaks for which a source type is to be determined, process 700 ends.

Figure 8:
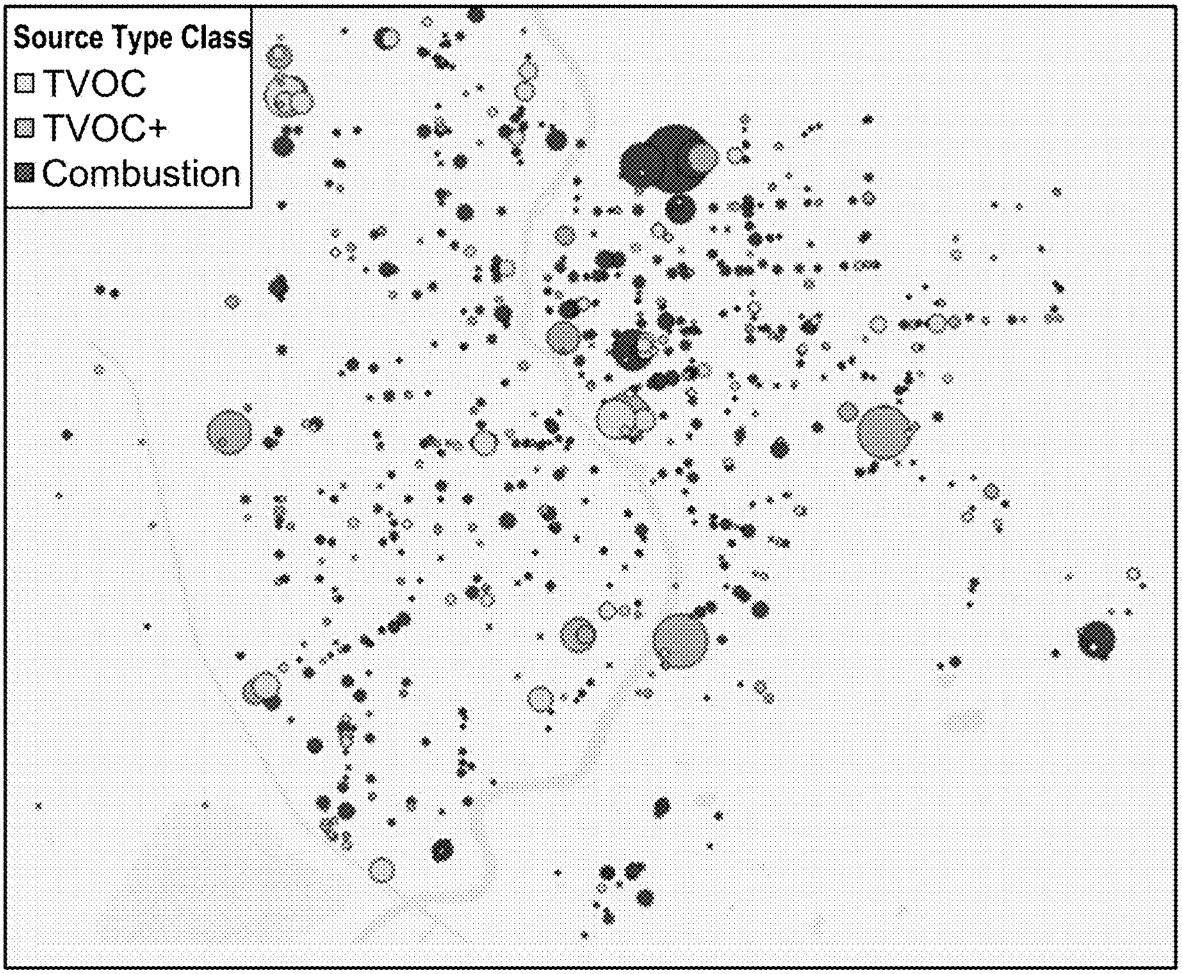
FIG. 8 is a diagram that indicates the location of the VOC (e.g., total VOCs) peaks detected in a first map region.

FIG. 8 is a diagram that indicates the location of the VOC (e.g., total VOCs) peaks detected in a first map region. Each circle represents a detected VOC peak. The location of each circle on the map is associated with the location of the represented VOC peak. The color/shade associated with each circle indicates the source type (e.g., TVOC, TVOC+, and Combustion) that to which the VOC peak has been classified. The size of each circle is indicative of the peak height (or strength) of the corresponding VOC peak.

Figure 9A:
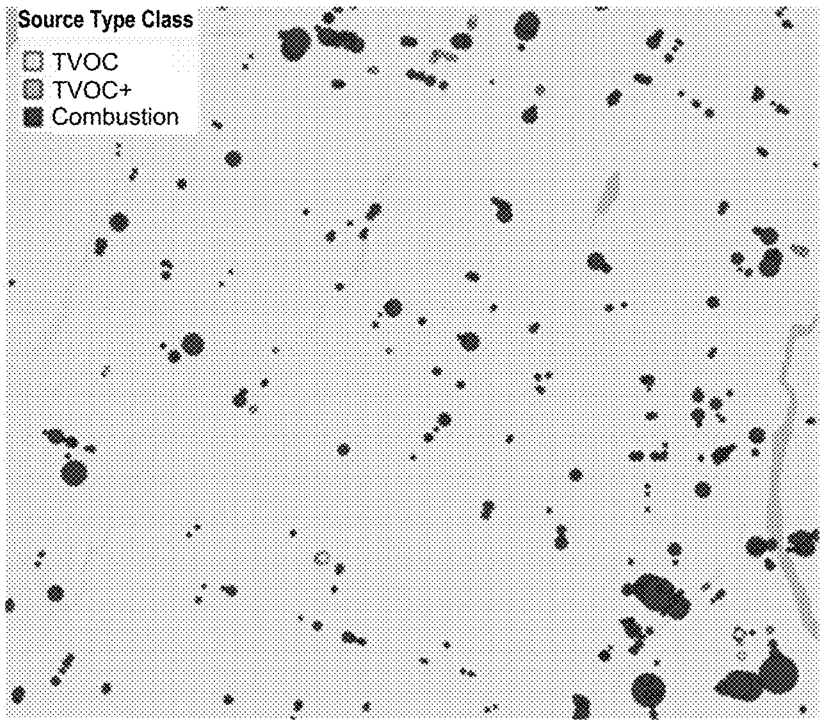
FIGS. 9A-9C depict various views for VOC data captured and analyzed in a second map region.
Figure 9B:
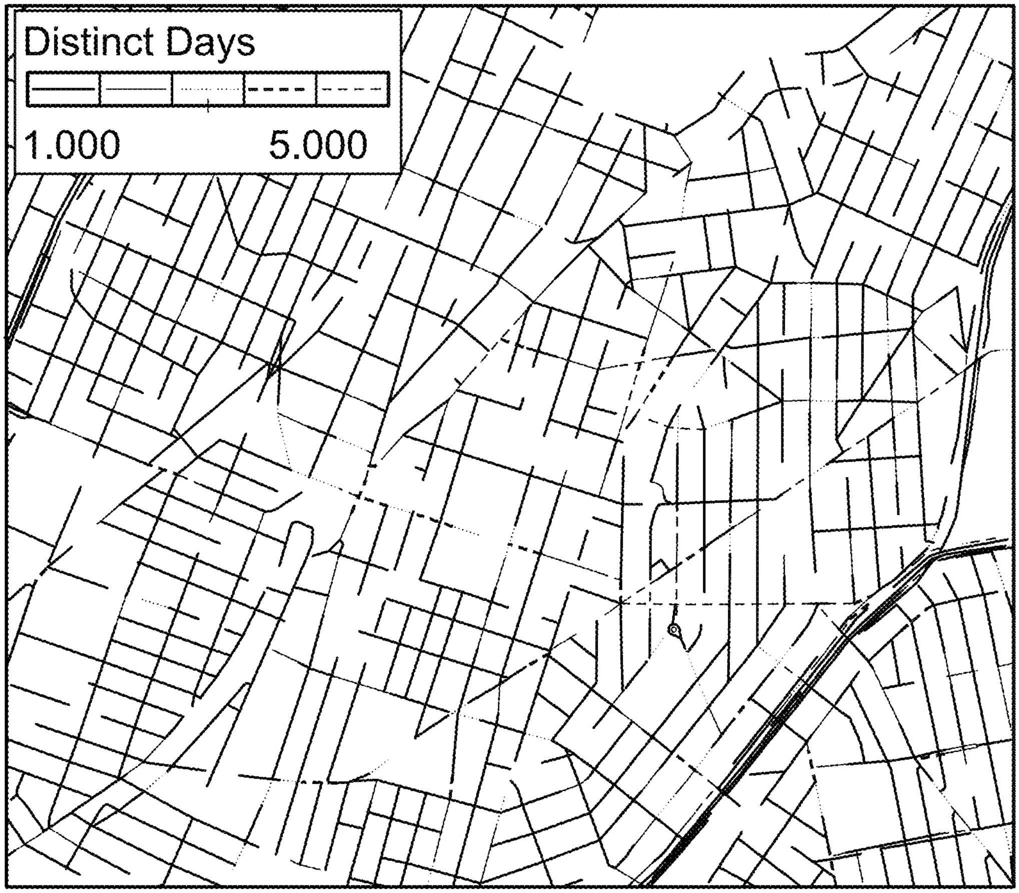
Figure 9C:
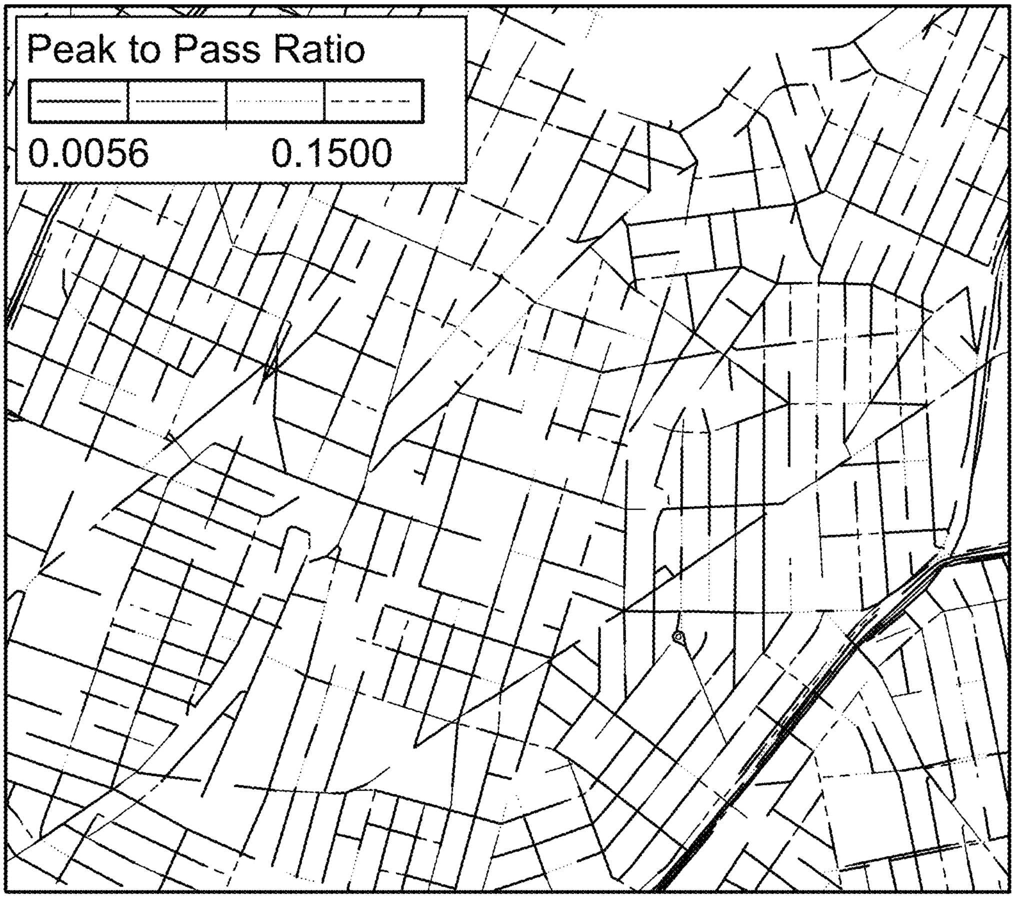

FIGS. 9A-9C depict various views for VOC data captured and analyzed in a second map region. FIG. 9A is a diagram that indicates the location of the VOC (e.g., total VOCs) peaks detected on various road segments in the second map region. Each circle represents a detected VOC peak. The location of each circle on the map is associated with the location of the represented VOC peak. The color/shade associated with each circle indicates the source type (e.g., TVOC, TVOC+, and Combustion) that to which the VOC peak has been classified. The size of each circle is indicative of the peak height (or strength) of the corresponding VOC peak. FIG. 9B is a closer view of a portion of the second region depicted in FIG. 9A. In FIG. 9B, the VOC peak locations are associated with road segments. Each road segment of FIG. 9B is labeled with a color/shade that matches the number of days on which at least one VOC peak has been detected on that segment within a given window of time. FIG. 9C is another closer view of a portion of the second region depicted in FIG. 9A. In FIG. 9C, the VOC peak locations are associated with road segments. Each road segment of FIG. 9C is labeled with a color/shade that matches the peak to pass ratio of VOC peaks that have been detected on that segment (e.g., within a given window of time). Thus, as shown in FIGS. 8 and 9A-9C, the collected VOC mobile sensor data may be associated with spatial/location-based presentations and therefore be more readily viewed and analyzed. As will be described below, in some embodiments, the individual VOC peaks may be clustered/aggregated into different spatial scales/spatial units (e.g., a hexagon-shaped grid cell or other shape of which the road segments on which data are accrued are part of) for further analysis and visualization.

Figure 10:
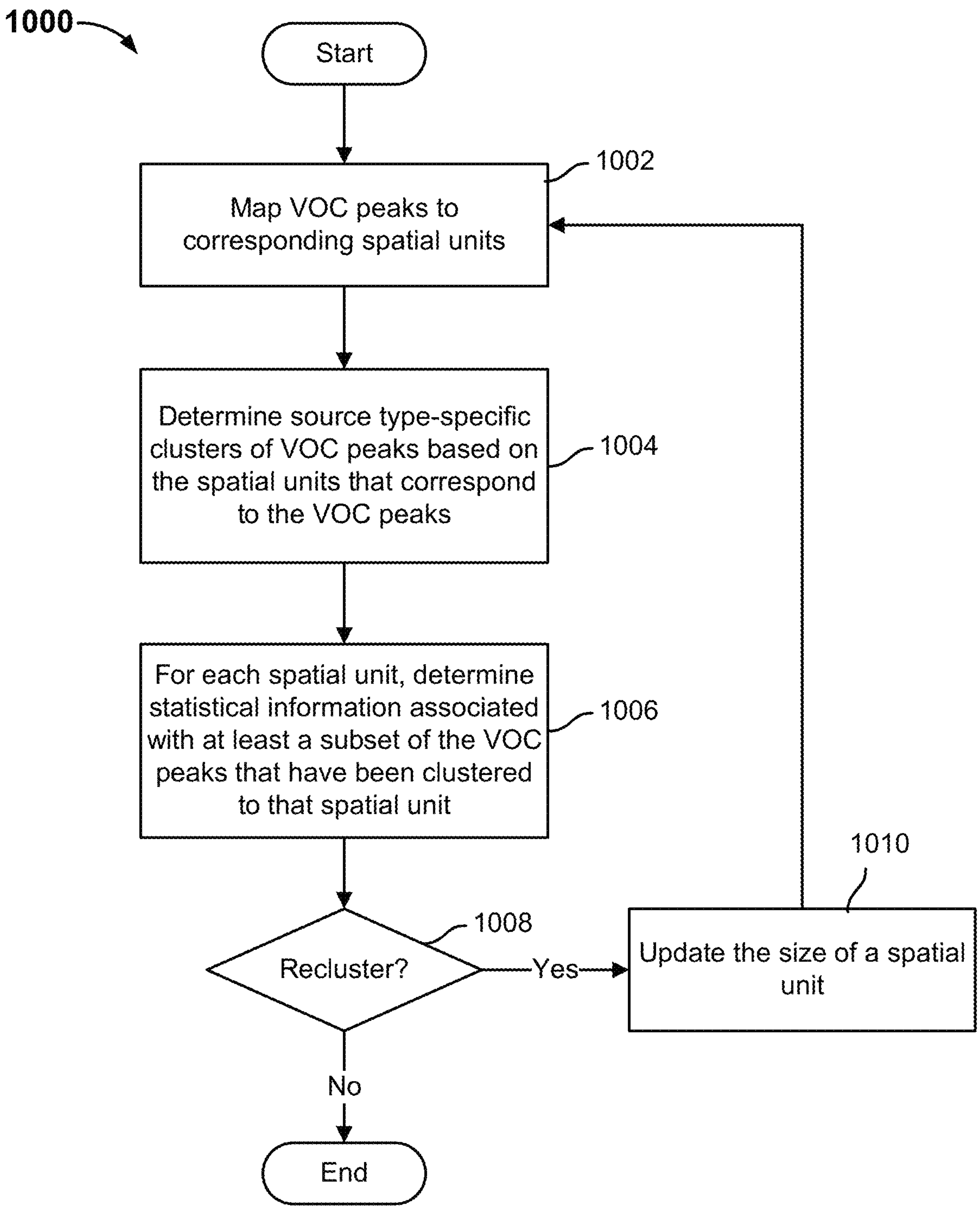
FIG. 10 depicts an exemplary embodiment of method 1000 for the clustering of VOC peaks according to spatial units to which the VOC peaks belong.

FIG. 10 depicts an exemplary embodiment of method 1000 for the clustering of VOC peaks according to spatial units to which the VOC peaks belong. Method 1000 is described in the context of system 100 of FIG. 1, but may be performed using other systems. Specifically, as described below, method 1000 may be carried out on multiple sensor systems, such as mobile sensor systems 102A, 102B and 102C and server 150. For clarity, only some portions of method 1000 are shown. Although shown in a sequence, in some embodiments, processes may occur in parallel and/or in a different order (including in parallel).

At 1002, VOC peaks are mapped to corresponding spatial units. In various embodiments, spatial units are defined across a region. Examples of spatial units include hexagon-shaped cells (e.g., hexbins), road segments, rectangles, or any other shape. In some embodiments, all spatial units across a region can share the same dimensions. For example, each hexagon-shaped cell can be 100 meters to 200 meters across. In some embodiments, spatial units across a region can have variable dimensions. As described above, each VOC peak is associated with metadata such as location information. As such, each VOC peak can be mapped to the spatial unit in which the VOC peak's location is located.

At 1004, source type-specific clusters of VOC peaks are determined based on the spatial units that correspond to the VOC peaks. As described above, the VOC peaks have also been classified into source types (e.g., using a process such as process 500 of FIG. 5). The source type classified VOC peaks are clustered based on the spatial units to which they have been mapped at step 1002. In some embodiments, all VOC peaks that have been mapped to the same spatial unit and share the same source type classification are part of the same cluster. In some embodiments, a source type-specific VOC peak cluster in one spatial unit may be merged with a VOC peak cluster of the same source type in one or more neighboring spatial units.

In some embodiments, the weighted centroid of the VOC peaks in a cluster is defined as the cluster location. The weight for each location is the enhancement (e.g., magnitude) of the peak at that location. Thus, the location of the cluster is more influenced by the largest peak in the cluster. Once VOC peaks are grouped into clusters, an area (e.g., a set of neighboring spatial units) encompassed by the cluster may also be defined. This may be accomplished by buffering the individual spatial units that include a portion of a cluster and combining these buffers into a single polygon. In some embodiments, this is parameterized with a buffer distance. In addition, other methods could be used to define the cluster area. For example, a bounding box or convex hull may be utilized, but may generally overestimate the cluster area.

At 1006, for each spatial unit, statistical information associated with at least a subset of the VOC peaks that have been clustered in that spatial unit is determined. Statistical information associated with all the VOC peaks that have been mapped to each spatial unit and the source type specific VOC peak clusters that are located within the spatial unit are determined. Examples of such per-spatial unit statistical information include the number of (any source type) VOC peaks that are located within the spatial unit and the respective percentage of each source type VOC peak (e.g., there is 70% combustion VOC peaks, 20% TVOC+VOC peaks, and 10% TVOC peaks) that have been clustered within the spatial unit.

In some embodiments, in addition to determining per-spatial unit statistics, statistics/metrics are also calculated for each cluster, as will be described in FIG. 12.

In some embodiments, a presentation of the spatial units across a region can be generated and where each spatial unit is represented to indicate at least one statistical attribute associated with the spatial unit.

At 1008, whether reclustering of the VOC peaks should be performed is determined. In the event that reclustering of the VOC peaks should be performed, control is transferred to 1010. Otherwise, in the event that reclustering of the VOC peaks should not be performed, process 1000 ends. The spatial unit statistics and/or the cluster statistics as described above, and the metrics regarding the number of spatial units/clusters that include VOC peaks can be compared to reclustering criteria to determine whether the VOC peaks should be reclustered across spatial units with updated sizes. For example, the reclustering criteria can determine whether the VOC peaks have been sufficiently spread across a desired distribution of spatial units to avoid an undesirable low (e.g., one) number of VOC peak cluster for each source type or avoid an undesirable high number of VOC peak cluster for each source type. Depending on whether the reclustering criteria is met, the spatial unit may be sized up or down. For example, if there are too few clusters that were formed in the previous clustering process, then the size of the spatial units can be decreased so that the VOC peaks would map across more spatial units and result in more clusters. Also, for example, if there are too many clusters that were formed in the previous clustering process, then the size of the spatial units can be increased so that the VOC peaks would map across fewer spatial units and result in fewer clusters.

At 1010, the size of a spatial unit is updated. The size of the spatial units are adjusted according to the reclustering criteria that was met at 1008 and the clustering process restarted at step 1002.

Figure 11:
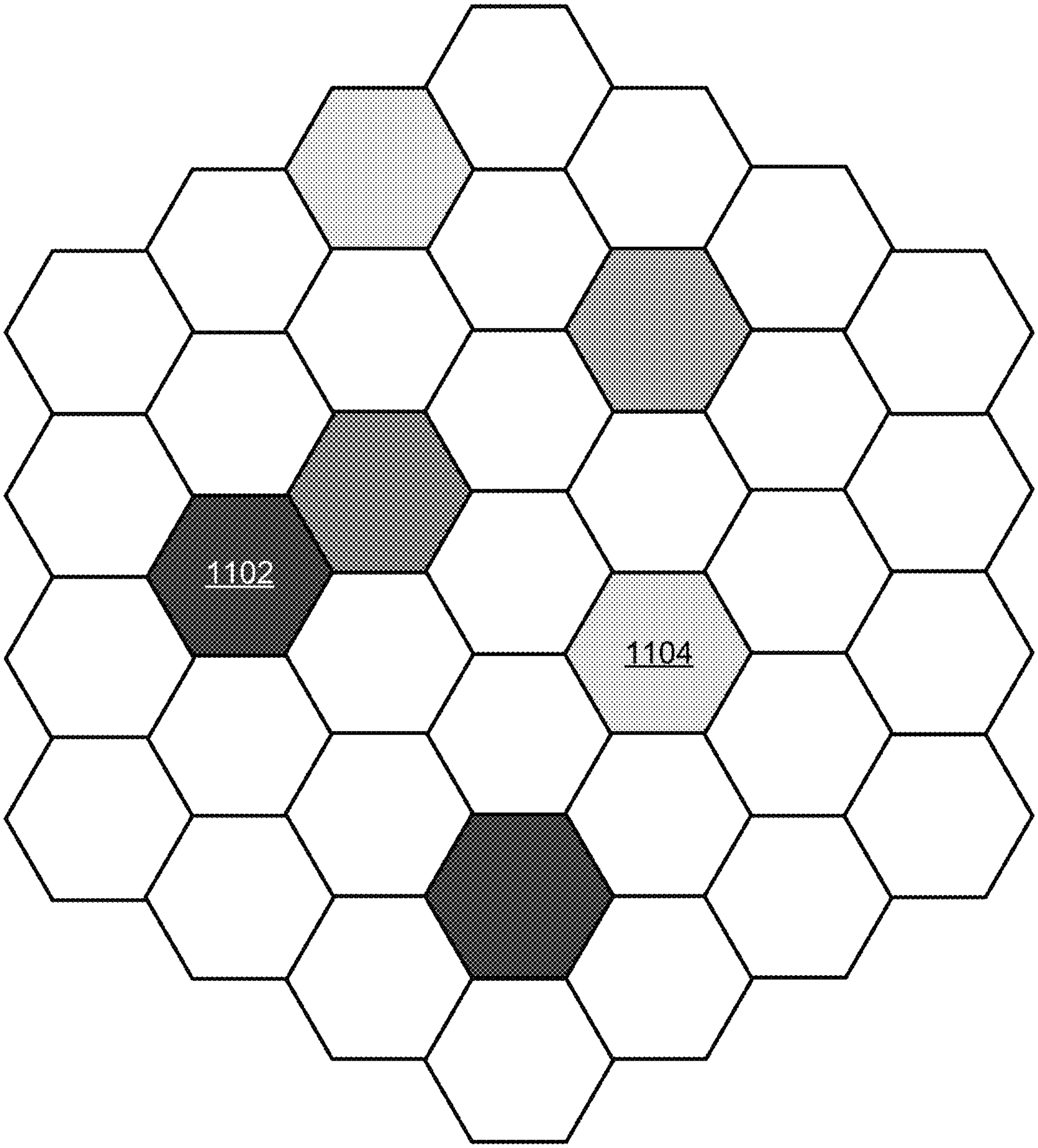
FIG. 11 is a diagram showing at least some spatial units across a particular region.

FIG. 11 is a diagram showing at least some spatial units across a particular region. In the example of FIG. 11, the region has been divided into spatial units that are hexagons. Each hexagon in the example of FIG. 11 is shown with a shade that represents the count of VOC peaks (of any source type) that are located within that hexagon and where the darker the shade, the more VOC peaks that are located within that hexagon. As such, hexagon 1102 is shown to include more VOC peaks than hexagon 1104.

While not shown in FIG. 11, the VOC peaks that are located within each hexagon can be separated into clusters based on the source types to which they have been classified. Also, statistical information related to the VOC peaks and/or their respective source type classifications can be determined on a per hexagon basis and, optionally, output at a user interface.

In some other embodiments, a clustering mechanism such as DBSCAN may be used. Thus, the clustering may be based on the minimum number of points in a VOC peak, the maximum distance between two VOC peaks for the peaks to be considered part of the same cluster, and the distance metric which is a measure of how the distances between samples are calculated. In some embodiments, the minimum number of points selected may be as small as three. In other embodiments, other minimum numbers of points might be used. The distance is the maximum distance between two VOC peaks for them to be considered part of the same cluster. In some embodiments, the distance is twenty-five meters. However, in other embodiments, other distances may be used. In some embodiments, the Haversine distance is used as the distance metric. Other measures may be used in other embodiments.

Figure 12:
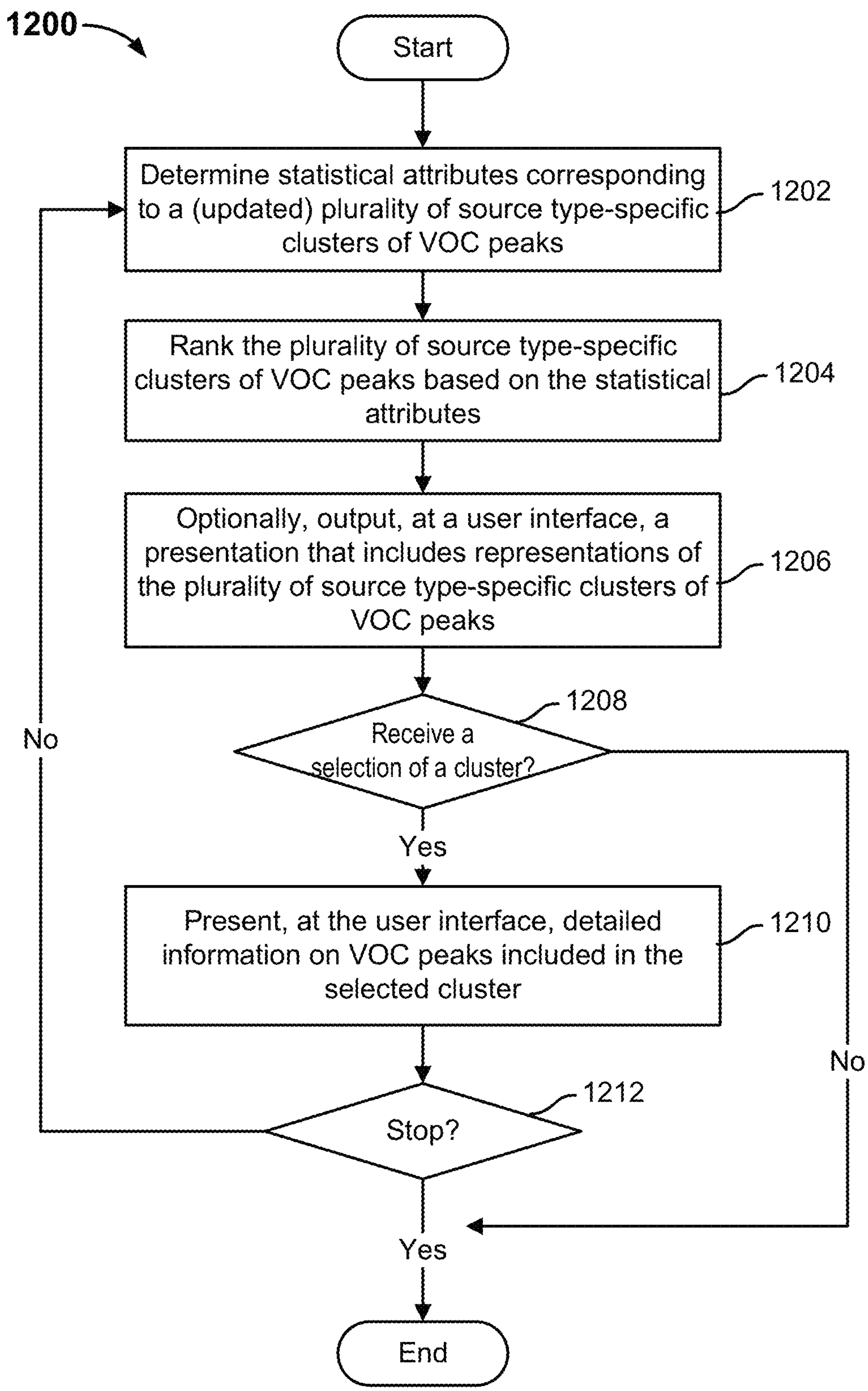
FIG. 12 depicts an exemplary embodiment of method 1200 for determining statistical attributes related to source type-specific clusters of VOC peaks.

FIG. 12 depicts an exemplary embodiment of method 1200 for determining statistical attributes related to source type-specific clusters of VOC peaks. Method 1200 is described in the context of system 100 of FIG. 1, but may be performed using other systems. Specifically, as described below, method 1200 may be carried out on multiple sensor systems, such as mobile sensor systems 102A, 102B and 102C and server 150. For clarity, only some portions of method 1200 are shown. Although shown in a sequence, in some embodiments, processes may occur in parallel and/or in a different order (including in parallel).

At 1202, statistical attributes corresponding to a plurality of source type-specific clusters of VOC peaks. As described above in process 1000 of FIG. 10, clusters of VOC peaks of respective source type classifications (e.g., TVOC, TVOC+, and combustion) are determined based on the spatial/location information of each VOC peak. As a result of such clustering, zero or more clusters of VOC peaks at proximate locations to each other (e.g., are located within the same or neighboring spatial units) and of the same VOC peak source type (e.g., TVOC, TVOC+, and combustion) are included in the same cluster. Statistical attributes are determined for each such cluster of source type-specific VOC peaks of a respective source type classification (e.g., TVOC, TVOC+, and combustion). Examples of statistical attributes that can be determined with respect to each source type-specific cluster include one or more of the following: the average peak height/strength of the VOC peaks of the cluster, the count of distinct days on which the VOC peaks in the cluster were detected, the average frequency of occurrence of VOC peaks of the cluster, sampling details, peak summaries, and source summaries. Sampling details provide descriptions of the cluster itself and information related to sampling effort. Peak summaries provide summary metrics of a few selected peak fields. Source summaries provide a summary of metrics related to the calculated/determined leak rate and distance estimated from the data. Additional and/or other metrics may be determined in other embodiments. In some embodiments, for example, the sampling details may include the peak count, the number of passes, the detection rate, the number of days having a peak, the number of days driven, the average enhancement for each peak, the enhancement standard of deviation, the average maximum values, the maximum standard of deviation, the time or number of passes since anything within the cluster has been detected, and the number of peaks within a cluster detected within a defined number of passes. For the peak count, the peak count includes the number of VOC peaks included in the cluster. A concurrent peak count may include the number of peaks where the VOC peak and another peak are concurrent (e.g., occurring at substantially the same time and location and, in some embodiments, which are correlated as described above). The number of passes is the number of times the vehicle(s) having mobile sensor platform(s) was/were driven through the cluster. Other and/or additional statistics may be determined in other embodiments.

At 1204, the plurality of source type-specific clusters of VOC peaks is ranked based on the statistical attributes. In some embodiments, clusters of the same source type can be ranked among themselves so that a respective ranked list of clusters is determined for each source type. For example, each source type-specific cluster can be scored as a function of its determined statistical attributes and where a higher score corresponds to a higher priority that is needed to address/further investigate the cluster (e.g., a more persistent location/source of VOC-related pollutants).

At 1206, a presentation that includes representations of the plurality of source type-specific clusters of VOC peaks is optionally output at a user interface. Optionally, representations of the source type-specific clusters of VOC peaks can be output at a user interface. For example, the presentation can include representations of the source type-specific clusters of VOC peaks on a map. In another example, the presentation can include ranked lists of clusters of VOC peaks according to their source type classifications.

At 1208, whether a selection of a cluster is selected is determined. In the event that a selection of a cluster is selected, control is transferred to 1210. Otherwise, in the event that a selection of a cluster is not selected, process 1200 ends. For example, a user selection of a particular source type-specific cluster can be made in the user interface displaying representations of the source type-specific clusters of VOC peaks on a map.

At 1210, detailed information on VOC peaks included in the selected cluster is presented. In response to a selection of the source type-specific cluster, additional information related to the cluster can be presented at the user interface. Examples of such additional information may include the statistical attributes that were determined at step 1202, a presentation that is determined based on the timestamps associated with the VOC peaks included in the cluster, and representations of a map of each individual VOC peak that is included in the cluster.

At 1212, whether updated clusters are to be determined. In the event that updated clusters are to be determined, control is returned to 1202. Otherwise, in the event that no more updated clusters are to be determined, process 1200 ends. Step 1202 can be returned in the event that updated clusters of source type-specific VOC peaks are determined.

Figure 13:
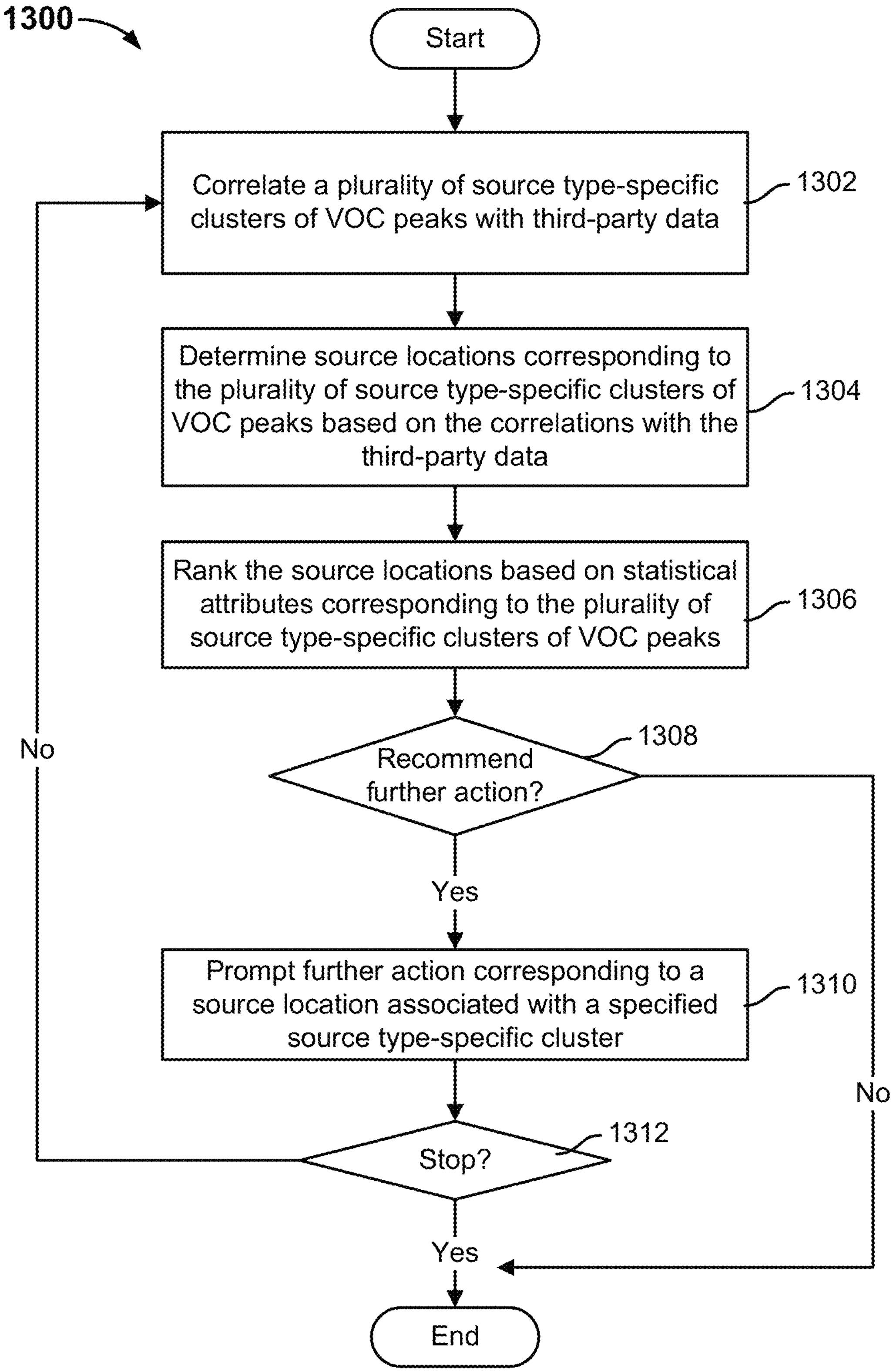
FIG. 13 depicts an exemplary embodiment of method 1300 for determining source locations corresponding to source type-specific clusters of VOC peaks.

FIG. 13 depicts an exemplary embodiment of method 1300 for determining source locations corresponding to source type-specific clusters of VOC peaks. Method 1300 is described in the context of system 100 of FIG. 1, but may be performed using other systems. Specifically, as described below, method 1300 may be carried out on multiple sensor systems, such as mobile sensor systems 102A, 102B and 102C and server 150. For clarity, only some portions of method 1300 are shown. Although shown in a sequence, in some embodiments, processes may occur in parallel and/or in a different order (including in parallel).

Process 1300 describes an example flow of inferring locations of sources that resulted in the VOC peaks of a cluster based on the cluster's correlation with third-party data (e.g., meteorological data). In other examples, locations of sources that resulted in the VOC peaks of a cluster can be determined based on other techniques.

At 1302, a plurality of source type-specific cluster of VOC peaks is correlated with third-party data. Examples of third-party data includes meteorological data. For example, the wind conditions during the period over which the VOC mobile sensor data was collected may be determined. In some embodiments, third-party meteorological data (e.g., prevailing winds) may be correlated with the VOC peaks of each cluster. This may aid in determining the direction to the source of VOC peaks (e.g., upwind) that belong to the same cluster. For example, in some embodiments, the wind direction may be located to within a quadrant (e.g., to within 90 degrees of a particular direction). In some embodiments, wind data may be sensed by the sensor system (e.g., mobile sensor systems 102) during its regular sensor data collection operations. Other data (e.g., temperatures, barometric pressure, precipitation, etc.) may also be correlated with each cluster's VOC peak data. Other examples of third-party data with which the VOC peaks can be correlated include sensor data from third-party fleets of mobile sensor platforms and/or data from remote sensing (e.g., satellite data).

At 1304, source locations corresponding to the plurality of source type-specific clusters of VOC peaks is determined based on the correlations with the third-party data. The clusters' correlations with third-party data such as, for example, meteorological data may be analyzed to detect, locate, and characterize the source locations of the VOC peaks associated with each source type-specific cluster. For example, identification of the source locations (e.g., combustion, non-combustion, or something else related), geographic proximity of the peaks to the source locations, wind direction and speed used to determine the source locations, vehicle direction and speed, peak intensity and other peak characteristics may be analyzed to determine for each source type-specific cluster, one or more potential source locations. For example, the VOC peaks' of a cluster's correlations with wind conditions may indicate that the VOC peaks are consistently downwind of a particular source location that has characteristics that match the cluster's source type (e.g., combustion). In some embodiments, source locations are determined from a predetermined list of businesses or a list of points of interest.

At 1306, the source locations is ranked based on statistical attributes corresponding to the plurality of source type-specific clusters of VOC peaks. Possible source locations corresponding to each cluster may be prioritized and ranked based on their priority. The priority of a source location represents, for example, the extent to which VOC peaks are persistent, strong, recent, and/or further attention at the source location is warranted. The priority of a source location may be determined, for example, by one or more of the following: the intensity of the VOC peaks, the number of VOC peaks in a given region, the peak-to-pass ratio (number of times a peak is detected divided by the total number of times a location was passed), the number of distinct days the peak is detected (or other measure of the frequency of detection), the persistence of detection (e.g., the number of consecutive distinct days the peak is detected), the (e.g., historical) emission rate of the source location, and whether the source location corresponds to a correctable emission source (e.g., a natural gas leak).

At 1308, whether further action is recommended is determined. In the event that the further action is recommended, control is transferred to 1310. Otherwise, in the event that the further action is not recommended, control is transferred to 1310. In some embodiments, further action is recommended on at least a portion of the source locations that have been determined for the source type-specific clusters of VOC peaks. For example, the source location(s) with priorities over a threshold priority are recommended for further action. In another example, the source location(s) corresponding to a predetermined number of highest priorities are recommended for further action.

At 1310, further action corresponding to a source location associated with a specified source type-specific cluster is prompted. To prompt for further action on a source location includes to send an alert to a client and/or present at a user interface a prompt that identifies the source location and the source type-specific cluster to which it corresponds. For example, further action may include deploying equipment with higher sensitivity and/or pollutant speciation ability to the region (e.g., the source location and/or location of the cluster) of persistent peaks. The speciation of pollutants (e.g., by canister sampling, gas chromatography, mass spectrometry, optical spectroscopy, etc.) provided by the deployment of such equipment for targeted surface may be utilized to further detect specific VOC pollutants (which is sometimes refer to as making speciated VOC measurements) and use that information to confirm the source location/reason of the VOCs. In some embodiments, the correlation with third-party (e.g., meteorological) data in combination with the speciation may be used to target and identify the specific source of VOC(s). Such higher sensitivity equipment may be significantly more expensive than mobile sensing systems 102 and may take longer to take individual measurements. Consequently, the identification of persistent VOC peaks and the correlation with other data (e.g., other pollutants and/or meteorological data) may provide an important trigger for such targeted surveys. This additional data provided by targeted surveys may also be used to draw additional conclusions such as whether emitters of VOCs are in compliance with the parameters of their permits, whether the emitters of VOCs are unpermitted, and/or whether mitigation actions are desired.

At 1312, whether updated clusters are to be determined. In the event that updated clusters are to be determined, control is returned to 1302. Otherwise, in the event that no more updated clusters are to be determined, process 1300 ends. Step 1302 can be returned in the event that updated clusters of source type-specific VOC peaks are determined.

Thus, as shown above in process 1300, the source locations corresponding to clusters of VOC peaks may be characterized over time. For example, the priority of the source location may be adjusted based upon changes to its characteristics, detection of new source locations and/or changes to other source locations.

Using process 1300, multiple sensor systems mounted on multiple vehicles and/or multiple passes over a region by the same vehicle may enhance detection of VOCs. Process 1300 may also be repeated over time internals using one or more systems. Thus, changes in the presence of VOC peaks may be determined. For example, the effectiveness of regulatory schemes and/or punishments may be determined. Thus, mitigation of the effects of VOCs and other emissions may be improved. Further, the cost of sources such as VOC leaks may also be reduced. These benefits may be achieved while passively and more efficiently collecting environmental data.

Figure 14:
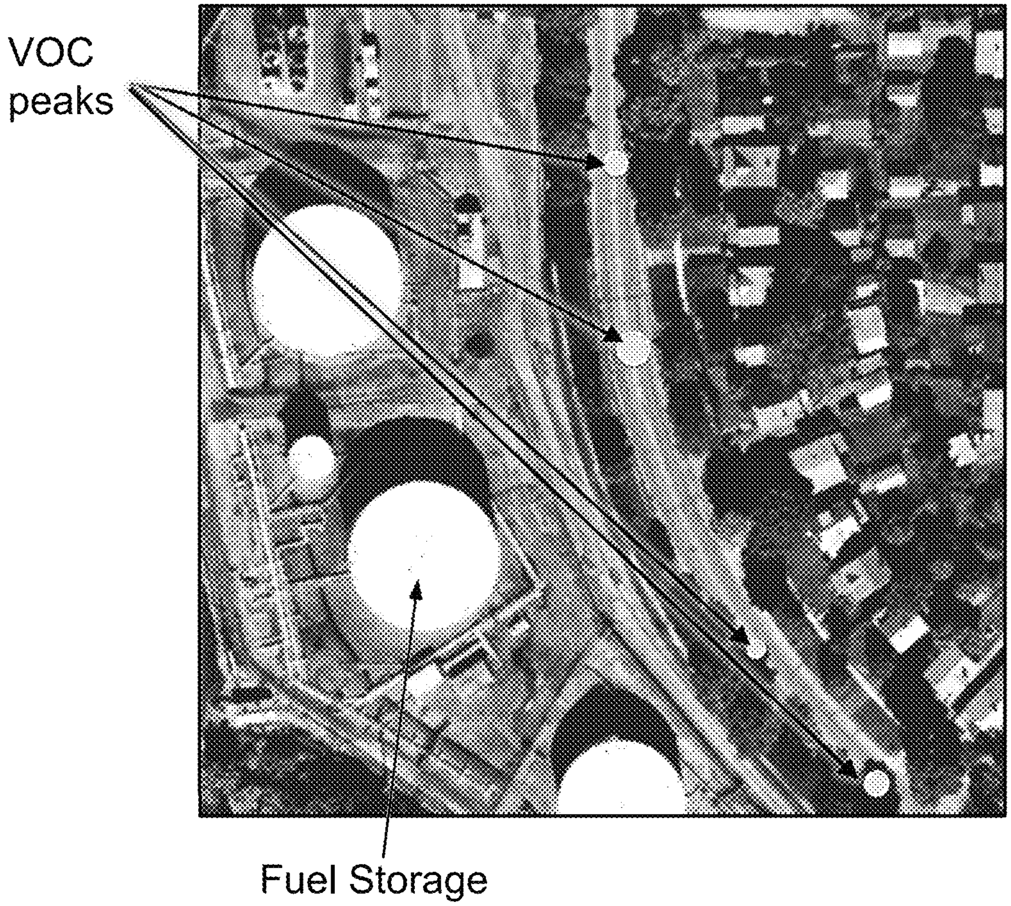
FIG. 14 is a diagram showing a satellite map depicting a closer view of VOC peaks (associated with the same cluster) detected on the same road segment on two distinct dates, indicating persistence of a VOC source over time in this location.

FIG. 14 is a diagram showing a satellite map depicting a closer view of VOC peaks (associated with the same cluster) detected on the same road segment on two distinct dates, indicating persistence of a VOC source over time in this location. The possible source location of the four shown VOC peaks may be identified as the fuel storage tanks in proximity to the peaks, as shown in the satellite map base layer. Thus, using system 100 and processes such as process 400 of FIG. 4, process 500 of FIG. 5, process 700 of FIG. 7, process 1000 of FIG. 10, process 1200 of FIG. 12, and/or process 1300 of FIG. 13, the source locations of VOC peaks of a cluster may be tentatively identified. More sensitive and/or pollutant speciation equipment may be deployed to confirm whether VOCs are leaking from the fuel storage tanks, identify the specific VOC pollutant(s) leaking, and propose and undertake mitigation measures.

In various embodiments, VOC mobile sensor data and non-VOC mobile sensor data are continuously collected and analyzed for peaks (e.g., using a process such as process 500 of FIG. 5). Data is collected on multiple sensor systems 102 mounted on multiple vehicles and/or by multiple passes over the same region by the same vehicle having a sensor system. For example, a fleet of vehicles, each of which includes one or more sensor systems 102, may be driven over routes and data passively collected. As previously indicated, the routes may be determined to map a particular area, to focus on a region at which a leak is predicted to occur, and/or for other purposes. In some embodiments, private individuals' vehicles may include sensor systems 102. Data collection occurs while the individuals use their vehicles in daily life. In some embodiments, a combination of a fleet of vehicles and private vehicles may be used. Data is collected passively on mobile platforms. For example, multiple vehicles may be used on the same day to collect data over a particular area. The data may also be collected (using the same or different routes) periodically. Thus, a time series of data to be captured for a region. For example, a particular location (e.g., a street segment or latitude/longitude defining the location) may be passed at least twice per month, and/or at least twenty times per year. Other total numbers of passes, frequencies of passes, and/or data collection periods may be used.

The data from the multiple sensor platforms 102 on multiple vehicles is analyzed to find peaks in various components, correlate the peaks, and identify the source type of VOC peak (e.g., combustion/non-combustion, TVOC+particular other constituent(s), TVOC only) (e.g., using a process such as process 700 of FIG. 7). Periodically or in response to a trigger, the current source type classified VOC peaks are clustered (e.g., using a process such as process 1200 of FIG. 12). In some embodiments, sensor platforms 102 upload data to server 150, which processes the data. Locations, times, shapes, and other data for the peaks may be determined in a manner analogous to that discussed with respect to method 400 of FIG. 4. Further, the persistence of the peaks may also be determined as part of process 1200 of FIG. 12 or process 1300 of FIG. 13. For example, the peak-to-pass ratio (the number of passes of a location for which a peak is identified divided by the total number of passes for the location), the number of distinct days for which a peak is identified at the location and/or other measures of the presence of the peak over time may be determined.

VOC detection as described herein provide analysis and correlation of VOC data (e.g., total VOCs). VOCs may be sensed at hyperlocal scales and analyzed. For example, total VOCs over a region may be rapidly sensed and tracked. As a result, potential VOC sources may be identified and tracked over time from the VOC data that is collected at scale, without any prior knowledge of candidate source locations of VOC emissions. Further, slower and more sensitive equipment may be more efficiently/selectively deployed (e.g., to areas with persistent VOC peaks). Thus, regulation, mitigation of leaks, and management of VOC emitters may be improved.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:

a processor configured to:

receive mobile sensor data, wherein the mobile sensor data includes volatile organic compounds (VOC) sensor data and non-VOC sensor data;

identify VOC peaks in the VOC sensor data;

identify non-VOC peaks in the non-VOC sensor data;

correlate the VOC peaks with the non-VOC peaks; and determine a source type associated with the VOC peaks based at least in part on the correlation between the VOC peaks and the non-VOC peaks; and a memory coupled to the processor and configured to provide the processor with instructions.

2. The system of claim 1, wherein the mobile sensor data is received from one or more mobile sensor platforms running at the same time over different routes over a predefined region.

3. The system of claim 2, wherein the mobile sensor platforms are mounted to mobile vehicles.

4. The system of claim 1, wherein the VOC sensor data is generated by a total VOC (TVOC) sensor.

5. The system of claim 1, wherein the VOC sensor data and the non-VOC sensor data comprise independent data streams.

6. The system of claim 1, wherein to identify the VOC peaks in the VOC sensor data comprises to determine whether measured VOC sensor data in a VOC sensor data stream exceeds a threshold.

7. The system of claim 6, wherein the threshold is determined based on a function of a rolling VOC sensor baseline within a sliding window applied to the VOC sensor data stream.

8. The system of claim 1, wherein to determine the source type associated with the VOC peaks comprises to:

determine that a VOC peak correlates with a combustive non-VOC peak; and determine that the VOC peak is associated with a combustion source type.

9. The system of claim 8, wherein the combustive non-VOC peak is associated with one of the following: carbon monoxide, carbon dioxide, and nitric oxide.

10. The system of claim 1, wherein to determine the source type associated with the VOC peaks comprises to:

determine that a VOC peak correlates with a non-combustive non-VOC peak; and determine that the VOC peak is associated with a non-combustion source type.

11. The system of claim 1, wherein to determine the source type associated with the VOC peaks comprises to:

determine that a VOC peak correlates with a neither a combustive non-VOC peak nor a non-combustive non-VOC peak; and determine that the VOC peak is associated with a VOC only source type.

12. The system of claim 1, wherein the processor is further configured to:

map the VOC peaks to corresponding spatial units;

determine source type-specific clusters of VOC peaks based on the spatial units corresponding to the VOC peaks; and determine, for a spatial unit, statistical information associated with at least a subset of the VOC peaks that have been clustered in the spatial unit.

13. The system of claim 12, wherein the spatial units comprise hexagon grid cells.

14. The system of claim 1, wherein the processor is further configured to:

determine statistical attributes corresponding to a plurality of source type-specific clusters of VOC peaks;

rank the plurality of source type-specific clusters of VOC peaks based on the statistical attributes;

receive a selection of a source type-specific cluster; and present, at a user interface, detailed information on VOC peaks included in the selected source type-specific cluster.

15. The system of claim 1, wherein the processor is further configured to:

correlate a plurality of source type-specific clusters of VOC peaks with third-party data;

determine source locations corresponding to the plurality of source type-specific clusters of VOC peaks based on the correlations with the third-party data;

rank the source locations based on statistical attributes corresponding to the plurality of source type-specific clusters of VOC peaks; and prompt further action corresponding to a source location associated with a specified source type-specific cluster based on the ranking.

16. The system of claim 15, wherein the further action includes generating speciated VOC measurements using an instrument that is more sensitive than a VOC sensor that was used to generate the VOC sensor data.

17. A method, comprising:

receiving mobile sensor data, wherein the mobile sensor data includes volatile organic compounds (VOC) sensor data and non-VOC sensor data;

identifying VOC peaks in the VOC sensor data;

identifying non-VOC peaks in the non-VOC sensor data;

correlating the VOC peaks with the non-VOC peaks; and determining a source type associated with the VOC peaks based at least in part on the correlation between the VOC peaks and the non-VOC peaks.

18. The system of claim 1, wherein the mobile sensor data is received from one or more mobile sensor platforms running at the same time over different routes over a predefined region.

19. The system of claim 1, wherein the VOC sensor data is generated by a total VOC (TVOC) sensor.

20. A computer program product, the computer program product is embodied in a non-transitory computer readable storage medium and comprising computer instructions:

receiving mobile sensor data, wherein the mobile sensor data includes volatile organic compounds (VOC) sensor data and non-VOC sensor data;

identifying VOC peaks in the VOC sensor data;

identifying non-VOC peaks in the non-VOC sensor data;

correlating the VOC peaks with the non-VOC peaks; and determining a source type associated with the VOC peaks based at least in part on the correlation between the VOC peaks and the non-VOC peaks.

* * * * *